(12) United States Patent
Sood et al.

(10) Patent No.: US 7,125,671 B2
(45) Date of Patent: *Oct. 24, 2006

(54) NUCLEIC ACID AMPLIFICATION WITH TERMINAL-PHOSPHATE LABELED NUCLEOTIDES

(75) Inventors: Anup Sood, Flemington, NJ (US); Shiv Kumar, Belle Mead, NJ (US); John Nelson, Hillsborough, NJ (US); Carl Fuller, Berkeley Heights, NJ (US); Anuradha Sekher, Monmouth Junction, NJ (US)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 408 days.

This patent is subject to a terminal disclaimer.

(21) Appl. No.: 10/651,362

(22) Filed: Aug. 29, 2003

(65) Prior Publication Data

US 2004/0152104 A1    Aug. 5, 2004

Related U.S. Application Data

(60) Provisional application No. 60/445,274, filed on Feb. 5, 2003.

(51) Int. Cl.
*C12Q 1/68* (2006.01)
*C12P 19/34* (2006.01)
(52) U.S. Cl. .................. 435/6; 435/91.1; 435/91.2
(58) Field of Classification Search ............ 435/6, 435/91.1, 91.2
See application file for complete search history.

(56) References Cited

U.S. PATENT DOCUMENTS 5,849,478 A    12/1998   Cashman 6,232,075 B1    5/2001   Williams
2003/0044781 A1*   3/2003   Korlach et al. ............ 435/6
2003/0064366 A1*   4/2003   Hardin et al. ............. 435/6
2006/0078937 A1*   4/2006   Korlach et al. ............ 435/6

FOREIGN PATENT DOCUMENTS

WO    WO 02/044425    6/2002
WO    WO 03/020891    3/2003
WO    WO 03/020984    3/2003

OTHER PUBLICATIONS

Dyatkina, N., et al., "Modified Triphosphates of Carbocyclic Nucleoside Analogues: Synthesis, Stability Towards Alkaline Phosphatase and Substrate Properties for some DNA Polymerases", *Bioorganic & Medicinal Chemistry Letters*, vol. 6, No. 22, 1996, p. 2639-2642.
Vassiliou, W., et al., "Exploiting Polymerase Promiscuity: A Simple Colorimetric RNA Polymerase Assay", *Virology*, vol. 274, 2000, p. 429-437.

* cited by examiner

*Primary Examiner*—Kenneth R. Horlick
(74) *Attorney, Agent, or Firm*—Yonggang Ji

(57) ABSTRACT

The present invention relates generally to the use of terminal-phosphate-labeled nucleotides having three or more phosphates as substrates for nucleic acid polymerases and their use in DNA amplification. The labels employed are chemiluminescent, fluorescent, electrochemical and chromogenic moieties as well as mass tags and include those that are directly detectable, detectable after enzyme activation or feed into other processes to generate a different signal. The signal generated from the attached dyes may also be used to quantify the amount of amplification. Further provided are stabilizers that enhance the stability of terminal-phosphate labeled nucleoside polyphosphates in aqueous solutions and are useful for reducing non-enzymatic hydrolysis of these nucleotides, hence decrease background.

30 Claims, 10 Drawing Sheets

SEQUENCE LISTING

<160> NUMBER OF SEQ ID NOS: 5

<210> SEQ ID NO 1
<211> LENGTH: 102
<212> TYPE: DNA
<213> ORGANISM: artificial sequence
<220> FEATURE:
<223> OTHER INFORMATION: PCR product

```
-continued

<400> SEQUENCE: 1
ctgtgcagct gtgggttgat tccacacccc cgcccggcac ccgcgtccgc            50
gccatggcca tctacaagca gtcacagcac atgacggagg ttgtgaggcg           100
ct                                                              102

<210> SEQ ID NO 2
<211> LENGTH: 22
<212> TYPE: DNA
<213> ORGANISM: artificial sequence
<220> FEATURE:
<223> OTHER INFORMATION: synthetic oligonucleotide

<400> SEQUENCE: 2
ctgtgcagct gtgggttgat tc                                         22

<210> SEQ ID NO 3
<211> LENGTH: 22
<212> TYPE: DNA
<213> ORGANISM: artificial sequence
<220> FEATURE:
<223> OTHER INFORMATION: synthetic oligonucleotide

<400> SEQUENCE: 3
agcgcctcac aacctccgtc at                                         22

<210> SEQ ID NO 4
<211> LENGTH: 18
<212> TYPE: DNA
<213> ORGANISM: artificial sequence
<220> FEATURE:
<223> OTHER INFORMATION: synthetic oligonucleotide

<400> SEQUENCE: 4
tgtaaaacga cggccagt                                              18

<210> SEQ ID NO 5
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 5
aggaaacagc tatgaccat                                             19
```

NUCLEIC ACID AMPLIFICATION WITH TERMINAL-PHOSPHATE LABELED NUCLEOTIDES

CROSS REFERENCE TO RELATED APPLICATIONS

This application claims priority to U.S. provisional application No. 60/445,274, filed Feb. 5, 2003; the disclosures of which are incorporated herein by reference in its entirety.

FIELD OF THE INVENTION

The present invention relates generally to nucleic acid amplification. More specifically, the present invention relates to the use of terminal-phosphate labeled nucleotides in nucleic acid amplification.

BACKGROUND OF THE INVENTION

Methods are known for detecting specific nucleic acids or analytes in a sample with high specificity and sensitivity. Such methods generally require first amplifying nucleic acid sequence based on the presence of a specific target sequence or analyte. Following amplification, the amplified sequences are detected and quantified. Conventional detection systems for nucleic acids include detection of fluorescent labels, fluorescent enzyme-linked detection systems, antibody-mediated label detection, and detection of radioactive labels.

One disadvantage of these methods is that the labeled product not only requires some type of separation from the labeled starting materials but also, since the label is attached to the product, it is different than the natural product to be identified. It would, therefore, be of benefit to use methods and substrates that form unmodified product and at the same time generate a signal characteristic of the reaction taking place. It is of further benefit if the signal generated doesn't require separation from the starting materials but even if a separation is required the benefits of generating unmodified product in many cases are overwhelming.

Terminal-phosphate labeled nucleotides provide the above benefits. For example, incorporation of gamma- or delta-labeled nucleotides into DNA or RNA by nucleic acid polymerases results in the production of unmodified DNA or RNA and at the same time the labeled pyrophosphate generated can be used to detect, characterize and/or quantify the target. If these could be used in amplification reactions not only would they provide useful tools for detection and quantification of target sequence, but the amplified product, which is exact copies of the target sequence without modifications can be used in further studies.

DNA amplification by a number of amplification methods is performed at high temperatures. For example, in PCR, repeated cycles of denaturation at 95° C., annealing around 60° C. and extension around 70° C. causes significant breakdown of the dNTP's. This may significantly affect the yield of product in later cycles. Other amplification methods such as RCA and NASBA, although isothermal, also are conducted at higher temperatures. In case of NASBA, which is performed at 41° C., the stability of nucleotides may not be very critical, however in RCA which may be conducted at higher temperature depending upon the polymerase used and the complexity of sequence to be amplified, stability of nucleotides can be an issue under these conditions. If breakdown of the terminal-phosphate labeled nucleotides were to occur, the amount of background generated would overwhelm any signal directly related to the amplification process. It is therefore desirable to have nucleotides that can survive this repeated cycling of temperature or prolonged heating at a constant yet high temperature and hence continue to give high product yields and low background even in later cycles of amplification and possibly cut down the number of cycles/time required to achieve desirable amplification. Additionally, gamma-phosphate labeled nucleotides are extremely poor substrates for polymerase under the conditions normally used for nucleic acid synthesis and amplification. Synthesis of long stretches of nucleic acids (several hundred to several thousand bases long) would require hours if not days per cycle. Harding et. al. (WO 0244425 A2) describe the use of aminonaphthalene-sulfonate-gamma-amido-dATP for DNA synthesis at high temperature. However, according to the inventors, in this case the synthesis only proceeds after the aminonaphthalenesulfonate hydrolyzes off the nucleotide and it is dATP that is used by the polymerase to form DNA. This of course is useless for detection or quantification of target sequence as the dye generated is independent of DNA synthesis.

A number of real time assays have been developed for quantification of DNA. Most of these can be classified into two categories. First category which is relatively easy to use involves the use of intercalating dyes, which have enhanced fluorescence upon intercalation. A number of nucleic acid stains such as ethidium bromide, SYBR Green® dyes, PicoGreen®, YOYO®, TOTO® or analogs have been developed as intercalators for real time assays. These, however, generate significant background signal partially due to intercalation between primer dimers and partially because they are fluorescent, albeit weakly, even when they are not intercalated.

The other category of real time assay is based on the use of fluorescence resonance energy transfer between a dye and a quencher. A number of these assays have been developed using FRET probes and or primers, such as Taqman, MGB Eclipse™, Scorpion primers, Molecular Beacons, sunrise primers, to name a few. These probes/primers are quenched by energy transfer until the amplification takes place and the quencher is physically separated from the dye or cleaved. Sensitivity of these assays depends greatly on the probe design and require a lot of optimization. In addition even with the best optimized probe, complete quenching is not achieved. So these assays can only provide a few fold enhancement in signal upon amplification and in the initial cycles background signal is much higher than the true signal.

It would be of benefit, therefore, to develop methods of amplification using terminal-phosphate labeled nucleoside polyphosphates where the amplification can be performed in reasonable time (similar to unmodified dNTP's) and the amount of label generated is proportional to the product formed. It is further desirable to have a real time assay, where the amount of label generated can be independently detected without interference of signal from the terminal-phosphate labeled nucleotide. It would be desirable to have a real time assay where the label is completely dark until the amplification proceeds.

SUMMARY OF THE INVENTION

The present invention provides methods of using terminal-phosphate labeled nucleotides (also referred to as terminal-phosphate labeled nucleoside polyphosphates) in nucleic acid amplification. Methods are also provided for the detection and quantification of a target sequence by selective amplification. Further provided are methods for the real-time detection and quantification of a target sequence during amplification.

The present invention provides for a method of detecting the presence of a nucleic acid sequence including the steps of: a) conducting a nucleic acid amplification which includes the reaction of a terminal-phosphate-labeled nucleotide, which reaction results in the production of labeled polyphosphate; b) permitting the labeled polyphosphate to react with a phosphatase to produce a detectable species; and c) detecting the presence of the detectable species. A definition of phosphatase in the current invention includes any enzyme which cleaves phosphate mono esters, phosphate thioester, phosphoramidate, polyphosphates and nucleotides to release inorganic phosphate. In the context of the present invention, this enzyme does not cleave a terminally labeled nucleoside phosphate (i.e. the terminal-phosphate-labeled nucleotide is substantially non-reactive to phosphatase). The phosphatase definition herein provided specifically includes, but is not limited to, alkaline phosphatase (EC 3.1.3.1) and acid phosphatase (EC 3.1.3.2). The definition of a nucleotide in the current invention includes a natural or modified nucleoside phosphate.

The present invention provides for a method of detecting the presence of a nucleic acid sequence including the steps of: a) conducting a nucleic acid amplification reaction in the presence of a manganese salt, wherein the reaction includes the reaction of a terminal-phosphate-labeled nucleotide, which reaction results in the production of labeled polyphosphate; b) permitting the labeled polyphosphate to react with a phosphatase to produce a detectable species; and c) detecting the presence of the detectable species.

The invention further provides for a method of detecting the presence of a DNA sequence including the steps of: a) conducting a DNA amplification reaction in the presence of a terminal-phosphate-labeled nucleotide, which reaction results in the production of a labeled polyphosphate; b) permitting the labeled polyphosphate to react with a phosphatase to produce a detectable species; and c) detecting the presence of the detectable species.

The invention further provides for a method of detecting the presence of a DNA sequence including the steps of: a) conducting a DNA amplification reaction in the presence of a terminal-phosphate-labeled nucleotide and a manganese salt, which reaction results in the production of a labeled polyphosphate; b) permitting the labeled polyphosphate to react with a phosphatase to produce a detectable species; and c) detecting the presence of the detectable species.

The invention further provides for a method of detecting the presence of a DNA sequence including the steps of: a) conducting a DNA amplification reaction in the presence of a terminal-phosphate-labeled nucleotide, which reaction results in the production of a labeled polyphosphate; b) detecting the presence of the labeled polyphosphate.

Also provided is a method of detecting the presence of a nucleic acid sequence comprising the steps of: (a) conducting a nucleic acid amplification reaction in the presence of at least one terminal-phosphate-labeled nucleotide having four or more phosphate groups in the polyphosphate chain, which reaction results in the production of a labeled polyphosphate; and (b) detecting the labeled polyphosphate.

Also provided is a method of detecting the presence of a nucleic acid sequence comprising the steps of: (a) conducting a nucleic acid amplification reaction in the presence of a manganese salt and at least one terminal-phosphate-labeled nucleoside polyphosphate, which reaction results in the production of a labeled polyphosphate; and (b) detecting the labeled polyphosphate.

Also provided is a method of detecting the presence of a nucleic acid sequence comprising the steps of: (a) conducting a nucleic acid amplification reaction in the presence of a manganese salt and at least one terminal-phosphate-labeled nucleotide having four or more phosphate groups in the polyphosphate chain, which reaction results in the production of a labeled polyphosphate; and (b) detecting the labeled polyphosphate.

In addition, the invention relates to a method of detecting the presence of a nucleic acid sequence comprising the steps of: (a) conducting a nucleic acid amplification reaction in the presence of at least one terminal-phosphate-labeled nucleotide having four or more phosphate groups in the polyphosphate chain, which reaction results in the production of a labeled polyphosphate; (b) permitting the labeled polyphosphate to react with a phosphatase to produce a detectable species; and (c) detecting the presence of the detectable species.

A further aspect of the present invention relates to a method of quantifying a nucleic acid including the steps of: (a) conducting a nucleic acid amplification reaction, wherein the reaction includes a terminal-phosphate-labeled nucleotide, which reaction results in production of labeled polyphosphate; (b) permitting the labeled polyphosphate to react with a phosphatase to produce a detectable by-product species in an amount substantially proportional to the amount of nucleic acid; (c) measuring the detectable species; and (d) comparing the measurements using known standards to determine the quantity of nucleic acid.

In addition, the invention relates to a method of detecting the presence of a nucleic acid sequence comprising the steps of: (a) conducting a nucleic acid amplification reaction in the presence of a manganese salt and at least one terminal-phosphate-labeled nucleotide having four or more phosphate groups in the polyphosphate chain, which reaction results in the production of a labeled polyphosphate; (b) permitting the labeled polyphosphate to react with a phosphatase to produce a detectable species; and (c) detecting the presence of the detectable species.

A further aspect of the present invention relates to a method of quantifying a nucleic acid including the steps of: (a) conducting a nucleic acid amplification reaction in the presence of a manganese salt, wherein the reaction includes a terminal-phosphate-labeled nucleotide, which reaction results in production of labeled polyphosphate; (b) permitting the labeled polyphosphate to react with a phosphatase to produce a detectable by-product species in an amount substantially proportional to the amount of nucleic acid; (c) measuring the detectable species; and (d) comparing the measurements using known standards to determine the quantity of nucleic acid.

The invention further relates to a method of quantifying a DNA sequence including the steps of: (a) conducting a DNA polymerase reaction in the presence of a manganese salt and a terminal-phosphate-labeled nucleotide, the reaction resulting in production of labeled polyphosphate; (b) permitting the labeled polyphosphate to react with a phosphatase to produce a detectable by-product species in amounts substantially proportional to the amount of the DNA sequence; (c) measuring the detectable species; and (d) comparing the measurements using known standards to determine the quantity of DNA.

The invention further relates to a method of quantifying a DNA sequence including the steps of: (a) conducting a DNA amplification reaction in the presence of a manganese salt and a terminal-phosphate-labeled nucleotide, the reaction resulting in production of labeled polyphosphate in amounts substantially proportional to the amount of the DNA sequence; (b) measuring the labeled polyphosphate; and (c) comparing the measurements using known standards to determine the quantity of DNA.

Another aspect of the invention relates to a method for determining the identity of a single nucleotide in a nucleic acid sequence, which includes the steps of: (a) conducting a nucleic acid amplification reaction in the presence of at least one terminal phosphate-labeled nucleotide, an allele specific primer, which reaction results in the production of labeled polyphosphate; (b) permitting the labeled polyphosphate to react with a phosphatase to produce a detectable species; (c) detecting the presence of the detectable species; and (d) identifying the nucleoside incorporated.

Another aspect of the invention relates to a method for determining the identity of a single nucleotide in a nucleic acid sequence, which includes the steps of: (a) conducting a nucleic acid amplification reaction in the presence of at least one terminal phosphate-labeled nucleotide, an allele specific primer and a manganese salt, which reaction results in the production of labeled polyphosphate; (b) permitting the labeled polyphosphate to react with a phosphatase to produce a detectable species; (c) detecting the presence of the detectable species; and (d) identifying the nucleoside incorporated.

Also provided is a method for determining the identity of a single nucleotide in a nucleic acid sequence including the following steps: (a) conducting a nucleic acid amplification reaction in the presence of at least one terminal-phosphate-labeled nucleotide having four or more phosphate groups in the polyphosphate chain, which reaction results in the production of labeled polyphosphate; (b) permitting the labeled polyphosphate to react with a phosphatase to produce a detectable species; (c) detecting the presence of said detectable species; and (d) identifying the nucleoside incorporated.

Also provided is a method for determining the identify of a single nucleotide in a nucleic acid sequence including the following steps: (a) conducting a nucleic acid amplification reaction in the presence of a manganese salt and at least one terminal-phosphate-labeled nucleotide having four or more phosphate groups in the polyphosphate chain, which reaction results in the production of labeled polyphosphate; (b) permitting the labeled polyphosphate to react with a phosphatase to produce a detectable species; (c) detecting the presence of said detectable species; and (d) identifying the nucleoside incorporated.

The present invention further provides a method of amplifying a nucleic acid sequence in the presence of a terminal-phosphate labeled nucleoside polyphosphate stabilizer such as polyol (glycerol, threitol, etc.), a polyether including cyclic polyethers, polyethylene glycol, organic or inorganic salts, such as ammonium sulfate, sodium sulfate, sodium molybdate, sodium tungstate, organic sulfonate, etc., in conjunction with a terminal-phosphate labeled nucleoside polyphosphate in the presence of a metal salt, such as manganese, magnesium, zinc, calcium or cobalt salts, to decrease the background signal generation in an enzymatic assay.

The present invention further includes a nucleic acid detection kit wherein the kit includes:
(a) at least one or more terminal-phosphate-labeled nucleotide according to Formula I:

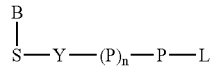

wherein P is phosphate (PO3) and derivatives thereof, n is 2 or greater; Y is an oxygen or sulfur atom; B is a nitrogen-containing heterocyclic base; S is a sugar moiety; L is a label containing a hydroxyl group, a sulfhydryl group, a haloalkyl group or an amino group suitable for forming a phosphate ester, a thioester, alkylphosphonate or a phosphoramidate linkage at the terminal phosphate of a natural or modified nucleotide; P-L is a phosphorylated label and may contain a linker between P and L; and
(b) at least one nucleic acid polymerase.

The present invention further includes a nucleic acid quantification kit wherein the kit includes:
(a) at least one terminal-phosphate-labeled nucleotide according to Formula below:

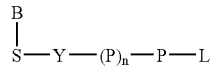

wherein P is phosphate (PO3) and derivatives thereof, n is 2 or greater; Y is an oxygen or sulfur atom; B is a nitrogen-containing heterocyclic base; S is a sugar moiety; L is an enzyme-activatable label containing a hydroxyl group, a sulfhydryl group, a haloalkyl group or an amino group suitable for forming a phosphate ester, a thioester, alkylphosphonate or a phosphoramidate linkage at the terminal phosphate of a natural or modified nucleotide; P-L is a phosphorylated label and may contain a linker between P and L; and
(b) at least one nucleic acid polymerase.

The present invention further includes a nucleic acid detection or quantification kit wherein the kit includes:
(a) at least one terminal-phosphate-labeled nucleotide according to Formula below:

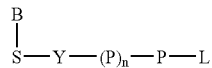

wherein P is phosphate (PO3) and derivatives thereof, n is 2 or greater; Y is an oxygen or sulfur atom; B is a nitrogen-containing heterocyclic base; S is a sugar moiety; L is an enzyme-activatable label containing a hydroxyl group, a sulfhydryl group or an amino group suitable for forming a phosphate ester, a thioester or a phosphoramidate linkage at the terminal phosphate of a natural or modified nucleotide; P-L is a phosphorylated label which preferably becomes independently detectable when the phosphate is removed;
(b) at least one nucleic acid polymerase;
(c) a phosphatase;
(d) a stabilizer; and
(e) a reaction buffer containing a manganese salt.

The present invention further includes a nucleic acid detection or quantification kit wherein the kit includes:
(a) at least one terminal-phosphate-labeled nucleotide according to Formula below:

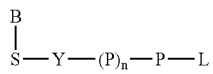

wherein P is phosphate (PO3) and derivatives thereof, n is 2 or greater; Y is an oxygen or sulfur atom; B is a nitrogen-containing heterocyclic base; S is a sugar moiety; L is an enzyme-activatable label containing a hydroxyl group, a sulfhydryl group or an amino group suitable for forming a phosphate ester, a thioester or a phosphoramidate linkage at the terminal phosphate of a natural or modified nucleotide; P-L is a phosphorylated label which preferably becomes independently detectable when the phosphate is removed; (b) at least one nucleic acid polymerase; and (c) phosphatase.

DETAILED DESCRIPTION OF THE PREFERRED EMBODIMENT

Figure 1:
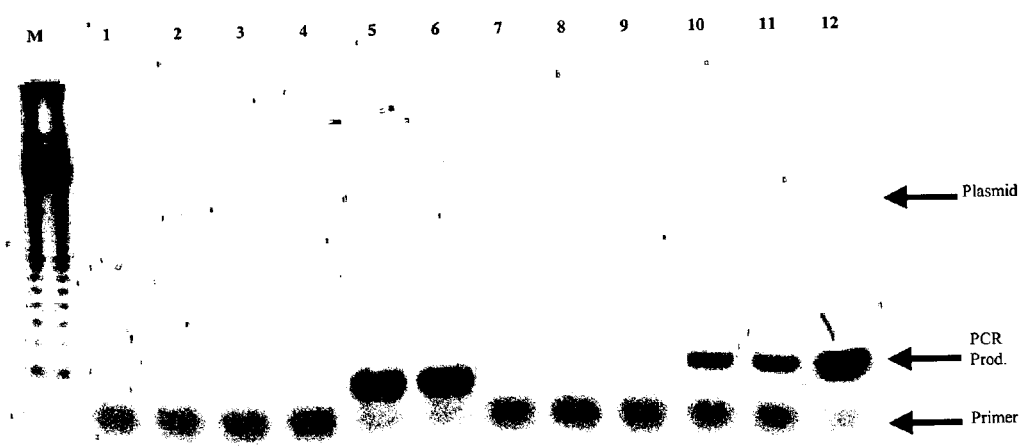
FIG. 1 is a gel showing PCR amplification of a target sequence using a terminal-phosphate labeled nucleoside polyphosphate with different polymerase.

The term "nucleoside" as defined herein is a compound including a purine deazapurine, pyrimidine or modified base linked to a sugar or a sugar derivative.

The term "nucleotide" as used herein refers to a phosphate ester of a nucleoside, wherein the esterification site typically corresponds to the hydroxyl group attached to the C-5 position of the pentose sugar.

The term "oligonucleotide" includes linear oligomers of nucleotides or derivatives thereof, including deoxyribonucleosides, ribonucleosides, and the like. Throughout the specification, whenever an oligonucleotide is represented by a sequence of letters, the nucleotides are in the 5'→3' order from left to right where A denotes deoxyadenosine, C denotes deoxycytidine, G denotes deoxyguanosine, and T denotes thymidine, unless noted otherwise.

The term "primer" refers to a linear oligonucleotide that anneals in a specific way to a unique nucleic acid sequence and allows for amplification of that unique sequence.

The phrase "target nucleic acid sequence" and the like refers to a nucleic acid whose sequence identity, or ordering or location of nucleosides is determined by one or more of the methods of the present invention.

The present invention relates to methods of detecting a polynucleotide in a sample wherein an assay is used for monitoring RNA or DNA synthesis via nucleic acid polymerase activity. RNA and DNA polymerases synthesize oligonucleotides via transfer of a nucleoside monophosphate from a nucleoside triphosphate (NTP) or deoxynucleoside triphosphate (dNTP) to the 3' hydroxyl of a growing oligonucleotide chain. The force which drives this reaction is the cleavage of an anhydride bond and the con-commitant formation of an inorganic pyrophosphate. The present invention utilizes the finding that structural modification of the terminal-phosphate of the nucleotide does not abolish its ability to function in the polymerase reaction. The oligonucleotide synthesis reaction involves direct changes only at the α- and β-phosphoryl groups of the nucleotide, allowing nucleotides with modifications at the terminal phosphate position to be valuable as substrates for nucleic acid polymerase reactions.

In certain embodiments, the polymerase is a DNA polymerase, such as DNA polymerase I, II, or III or DNA polymerase α, β, γ, or terminal deoxynucleotidyl transferase or telomerase. In other embodiments, suitable polymerases include, but are not limited to, a DNA dependent RNA polymerase, a primase, or an RNA dependant DNA polymerase (reverse transcriptase).

The methods provided by this invention utilize a nucleoside polyphosphate, such as a nucleoside polyphosphate, deoxynucleoside polyphosphate, with an electrochemical label, mass tag, or a colorimetric dye, chemiluminescent, or fluorescent label attached to the terminal-phosphate. When a nucleic acid polymerase uses this analogue as a substrate, a label would be present on the inorganic polyphosphate by-product of phosphoryl transfer. This label may be read directly or in preferable cases label is enzyme activatable and can be read after removal of phosphates. In latter case, cleavage of the polyphosphate product of phosphoryl transfer via phosphatase, leads to a detectable change in the label attached thereon. It is noted that while RNA and DNA polymerases are able to recognize nucleotides with modified terminal phosphoryl groups, the inventors have determined that this starting material is not a template for phosphatases. The scheme below shows some relevant molecules in the methods of this invention; namely the terminal-phosphate-labeled nucleotide, the labeled polyphosphate by-product and the enzyme-activated label.

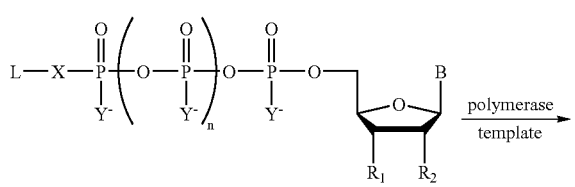

-continued

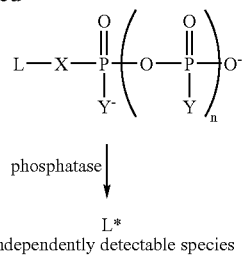

In the scheme above, n is 1 or greater, R1 is OH and R2 is H or OH; B is a nucleoside base or modified heterocyclic base; X is O, S, CH2 or NH; Y is O, S, or BH3; and L is a phosphatase activatable label which may be a chromogenic, fluorogenic, chemiluminescent molecule, mass tag or electrochemical tag. A mass tag is a small molecular weight moiety suitable for mass spectrometry that is readily distinguishable from other components due to a difference in mass. An electrochemical tag is an easily oxidizable or reducible species. It has been discovered that when n is 2 or greater, the nucleotides are significantly better substrates for polymerases than when n is 1. Therefore, in preferred embodiments, n is 2, 3 or 4; X and Y are O; B is a nucleoside base and L is a label which may be a chromogenic, fluorogenic or a chemiluminescent molecule.

In one embodiment of the method of detecting the presence of a nucleic acid sequence provided herein, the steps include (a) conducting a nucleic acid amplification reaction wherein the reaction includes at least one nucleotide which is substantially non-reactive to phosphatase in addition to one terminal-phosphate-labeled nucleotide wherein the polymerase reaction results in the production of labeled polyphosphate; (b) permitting the labeled polyphosphate to react with a phosphatase suitable to hydrolyze the phosphate ester and to produce a detectable species; and c) detecting the presence of a detectable species by suitable means. In this embodiment, the template used for the nucleic acid polymerase reaction may be a heteropolymeric or homopolymeric template. By terminal-phosphate-labeled nucleotide, it is meant throughout the specification that the labeled polyphosphate con-committantly released following incorporation of the nucleoside monophosphate into the growing nucleotide chain, may be read directly or if an enzyme-activatable label, it may be reacted with a phosphatase to produce a detectable species. Other nucleotides included in the reaction which are substantially non-reactive to phosphatase may also be, for example, blocked at the terminal-phosphate by a moiety which does not lead to the production of a detectable species by the method used for the detection of the detectable species produced from the labeled nucleotide. The nucleic acid for detection in this particular embodiment may include RNA, a natural or synthetic oligonucleotide, mitochondrial or chromosomal DNA.

In one embodiment of the method of detecting the presence of a nucleic acid sequence provided herein, the steps include (a) conducting a nucleic acid amplification reaction in the presence of a Mn salt wherein the reaction includes at least one nucleotide which is substantially non-reactive to phosphatase in addition to one terminal-phosphate-labeled nucleotide wherein the polymerase reaction results in the production of labeled polyphosphate; (b) permitting the labeled polyphosphate to react with a phosphatase suitable to hydrolyze the phosphate ester and to produce a detectable species; and c) detecting the presence of a detectable species by suitable means.

The invention further provides a method of detecting the presence of a DNA sequence including the steps of (a) conducting a DNA amplification reaction in the presence of a terminal-phosphate labeled nucleotide, which reaction results in the production of a labeled polyphosphate; (b) permitting the labeled polyphosphate to react with a phosphatase to produce a detectable species; and (c) detecting the presence of said detectable species. The DNA sequence for detection may include DNA isolated from cells, chemically treated DNA such as bisulfite treated methylated DNA or DNA chemically or enzymatically synthesized according to methods known in the art. Such methods include PCR, and those described in DNA Structure Part A: Synthesis and Physical analysis of DNA, Lilley, D. M. J. and Dahlberg, J. E. (Eds.), Methods Enzymol., 211, Academic Press, Inc., New York (1992), which is herein incorporated by reference. The DNA sequence may further include chromosomal DNA and natural or synthetic oligonucleotides. The DNA may be either double- or single-stranded.

The invention further provides a method of detecting the presence of a DNA sequence including the steps of (a) conducting a DNA amplification reaction in the presence of a Mn salt and a terminal-phosphate labeled nucleotide, which reaction results in the production of a labeled polyphosphate; (b) permitting the labeled polyphosphate to react with a phosphatase to produce a detectable species; and (c) detecting the presence of said detectable species.

The methods of the invention may further include the step of including one or more additional detection reagents in the polymerase reaction. The additional detection reagent may be capable of a response that is detectably different from the detectable species. For example, the additional detection reagent may be an antibody.

Suitable nucleotides for addition as substrates in the polymerase reaction include nucleoside polyphosphates, including, but not limited to, deoxyribonucleoside polyphosphates, ribonucleoside polyphosphates, and analogs thereof. Particularly desired are nucleotides containing 3, 4, or 5 phosphate groups in the polyphosphate chain, where the terminal phosphate is labeled.

It is noted that, it is within the contemplation of the present invention that the labeled polyphosphate by-product of phosphoryl transfer may be detected without the use of phosphatase treatment. For example, it is known that natural or modified nucleoside bases, particularly guanine, can cause quenching of fluorescent markers. Therefore, in a terminal-phosphate-labeled nucleotide, the label may be partially quenched by the base. Upon incorporation of the nucleoside monophosphate, the label of polyphosphate by-product may be detected due to its enhanced fluorescence. Alternatively, it is possible to physically separate the labeled polyphosphate product by chromatographic or other separation methods before identification by fluorescence, color, chemiluminescence, or electrochemical detection. In addition, mass spectrometry could be used to detect the products by mass difference.

The methods of the present invention may include conducting the polymerase reaction in the presence of at least one of DNA or RNA polymerase. Suitable nucleic acid polymerases may also include primases, telomerases, terminal deoxynucleotidyl transferases, and reverse transcriptases. A nucleic acid template may be required for the polymerase reaction to take place and may be added to the polymerase reaction solution. It is anticipated that all of the steps (a), (b) and (c) in the detection methods of the present invention could be run concurrently using a single, homogenous reaction mixture, as well as run sequentially.

Examples of amplification methods useful in the current invention include, but are not limited to, polymerase chain reaction (PCR), rolling circle amplification (RCA), strand displacement amplification (SDA), and nucleic acid sequence based amplification (NASBA). For e.g., wherein the target molecule is a nucleic acid polymer such as DNA, it may be detected by PCR incorporation of a gamma-phosphate labeled nucleotide base such as adenine, thymine, cytosine, guanine or other nitrogen heterocyclic bases into the DNA molecule. The polymerase chain reaction (PCR) method is described by Saiki et al in Science Vol. 239, page 487, 1988, Mullis et al in U.S. Pat. No. 4,683,195 and by Sambrook, J. et al. (Eds.), Molecular Cloning, second edition, Cold Spring Harbor Laboratory Press, Cold Spring Harbor, N.Y. (1980), Ausubel, F. M. et al. (Eds.), Current Protocols in Molecular Biology, John Wiley & Sons, Inc., NY (1999), and Wu, R. (Ed.), Recombinant DNA Methodology II, Methods in Zumulogy, Academic Press, Inc., NY, (1995). Using PCR, the target nucleic acid for detection such as DNA is amplified by placing it directly into a reaction vessel containing the PCR reagents and appropriate primers. Typically, a primer is selected which is complimentary in sequence to at least a portion of the target nucleic acid.

It is noted that nucleic acid amplification reactions suitable for conducting step (a) of the methods of the present invention may further include various RCA methods of amplifying nucleic acid sequences. For example, those disclosed in U.S. Pat. No. 5,854,033 to Lizardi, Paul M., incorporated herein by reference, are useful. Polymerase reactions may further include the nucleic acid sequence based amplification (NASBA) wherein the system involves amplification of RNA, not DNA, and the amplification is iso-thermal, taking place at one temperature (41° C.). Amplification of target RNA by NASBA involves the coordinated activities of three enzymes: reverse transcriptase, RNAse H, and T7 RNA polymerase along with oligonucleotide primers directed toward the sample target RNA. These enzymes catalyze the exponential amplification of a target single-stranded RNA in four steps: extension, degradation, DNA synthesis and cyclic RNA amplification.

Methods of RT-PCR, RCA, and NASBA generally require that the original amount of target nucleic acid is indirectly measured by quantification of the amplification products. Amplification products are typically first separated from starting materials via electrophoresis on an agarose gel to confirm a successful amplification and are then quantified using any of the conventional detection systems for a nucleic acid such as detection of fluorescent labels, enzyme-linked detection systems, antibody-mediated label detection and detection of radioactive labels. In contrast, the present method eliminates the need to separate products of the polymerase reaction from starting materials before being able to detect these products. For example, in the present invention, a reporter molecule (fluorescent, chemiluminescent or a chromophore) or other useful molecule is attached to the nucleotide in such a way that it is undetectable under certain conditions when masked by the phosphate attachment. However, following the incorporation of the nucleotide into the growing oligonucleotide chain and phosphatase treatment of the reaction, the label is detectable under those conditions. For example, if the hydroxyl group on the side of the triple ring structure of 1,3-dichloro-9,9-dimethyl-acridine-2-one (DDAO) is attached to the terminal-phosphate position of the nucleotide, the DDAO does not fluoresce at 659 nm. Once the nucleoside monophosphate is incorporated into DNA, the other product, DDAO polyphosphate (which also does not fluoresce at 659 nm) is a substrate for phosphatase. Once de-phosphorylated to form DDAO, the dye moiety will become fluorescent at 659 nm and hence detectable. The specific analysis of the polyphosphate product can be carried out in the polymerase reaction solution, eliminating the need to separate reaction products from starting materials. This scheme allows for the detection and, optionally, quantification of nucleic acids formed during polymerase reactions using routine instrumentation such as spectrophotometers.

In the methods described above, the amplification reaction step may further include conducting the polymerase reaction in the presence of a phosphatase, which converts labeled polyphosphate by-product to the detectable label. As such, a convenient assay is established for detecting the presence of a nucleic acid sequence that allows for continuous monitoring of detectable species formation. This represents a homogeneous assay format in that it can be performed in a single tube.

One format of the assay methods described above may include, but is not limited to, conducting the amplification reaction in the presence of a single type of terminal-phosphate-labeled nucleotide capable of producing a detectable species. For example, one could use a dye-labeled ATP while the remaining three nucleotides have a moiety that is not a dye; said moiety makes these nucleotides non-reactive towards phosphatase. In this example, the said moieties are not detectable under the conditions used for detecting said dye.

In another assay format, the amplification reaction may be conducted in the presence of more than one type of terminal-phosphate-labeled nucleotide, each type capable of producing a uniquely detectable species. For example, the assay may include a first nucleotide (e.g., adenosine polyphosphate) that is associated with a first label which when liberated enzymatically from the inorganic polyphosphate by-product of phosphoryl transfer, emits light at a first wavelength and a second nucleotide (e.g., guanosine polyphosphate) associated with a second label that emits light at a second wavelength. Desirably, the first and second wavelength emissions have substantially little or no overlap. It is within the contemplation of the present invention that multiple simultaneous assays based on nucleotide sequence information can thereafter be derived based on the particular label released from the polyphosphate.

In one aspect of the methods of detecting the presence of a nucleic acid sequence described above, the terminal-phosphate-labeled nucleotide may be represented by the following structure:

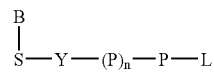

wherein P=phosphate (PO3) and derivatives thereof, n is 2 or greater; Y is an oxygen or sulfur atom; B is a nitrogen-containing heterocyclic base; S is a sugar moiety; L is an enzyme-activatable label containing a hydroxyl group, a sulfhydryl group or an amino group suitable for forming a phosphate ester, a thioester, or a phosphoramidate linkage at the terminal phosphate of a natural or modified nucleotide; P-L is a phosphorylated label which preferably becomes independently detectable when the phosphate is removed.

In another aspect, L may also contain a haloalkyl group suitable for forming alkyl phosphonate. In this aspect, labeled phosphate or labeled polyphosphate is the detectable species.

In certain embodiments, the sugar moiety in Formula I may be selected from the following: ribosyl, 2'-deoxyribosyl, 2'-alkoxyribosyl, 2'-aminoribosyl, 2'-fluororibosyl, and other modified sugars with the proviso that such modification doesn't prevent further nucleic acid chain elongation. For example, 3' position of the sugar must have a hydroxyl group so that incoming nucleoside monophosphate can attach to this position.

Moreover, in Formula I, the base may include uracil, thymine, cytosine, 5-methylcytosine, guanine, 7-deazaguanine, hypoxanthine, 7-deazahypoxanthine, adenine, 7-deazaadenine, 2,6-diaminopurine or analogs thereof.

The label attached at the terminal-phosphate position in the terminal-phosphate-labeled nucleotide may be selected from the group consisting of 1,2-dioxetane chemiluminescent compounds, fluorogenic dyes, chromogenic dyes, mass tags and electrochemical tags. This would allow the detectable species to be detectable by the presence of any one of color, fluorescence emission, chemiluminescence, mass change, electrochemical detection or a combination thereof.

In addition energy transfer dyes made by conjugating a donor dye and an acceptor dye are also useful in the current invention.

Examples of labels that may be attached to the terminal phosphate group either directly or through linkers are give in Tables 1–2 below. Some examples of terminal phosphate labeled nucleoside polyphosphates are shown in Table 3.

TABLE 1

Examples of detectable label moieties that become independently detectable after removal of phosphate residues 9H-(1,3-dichloro-9,9-dimethyl-7-hydroxyacridin-2-one)
9H-(9,9-dimethyl-7-hydroxyacridin-2-one)
9H-(1,3-dibromo-9,9-dimethyl-7-hydroxyacridin-2-one)
Resorufin
Umbelliferone (7-hydroxycoumarin)
4-Methylumbelliferone
4-Trifluoromethylumbelliferone
3-Cyanoumbelliferone
3-Phenylumbelliferone
3,4-Dimethylumbelliferone
3-Acetylumbelliferone
6-Methoxyumbelliferone
SNAFL ™
Fluorescein-alkyl ether TABLE 1-continued Examples of detectable label moieties that become independently detectable after removal of phosphate residues Naphthofluorescein
Naphthofluorescein alkyl ether
SNARF ™
Rhodol green ™
meso-Hydroxymonocarbocyanine
meso-Hydroxytricarbocyanine
meso-Hydroxydicarbocyanine
bis-(1,3-dibutylbarbituric acid)pentamethine Oxonol
1-Ethyl-2-(naphthyl-1-vinylene)-3,3-dimethyl-4-(3H)-6-indolinium salt
2-Hydroxy-5'-chloro-phenyl-chloro-quinazolone
Trifluoroacetyl-R110
Acetyl-R110
8-Hydroxy-2H-dibenz(b,f)azepin-2-one
8-hydroxy-11,11-dimethyl-11H-dibenz(b,e)(1,4)oxazepin-2-one
Hydroxypyrene
2-hydroxy-11,11-dimethyl-11H-dibenz(b,e)(1,4)oxazepin-8-one

TABLE 2

Examples of detectable moieties that are detectable even when attached to the nucleoside polyphosphate Rhodamine green carboxylic acid
Carboxy-fluorescein
Pyrene
Dansyl
Bodipy
Dimethylamino-coumarin carboxylic acid
Eosin-5-isothiocyanate
Methoxycoumarin carboxylic acid
Texas Red
Oregon Green ™ 488 carboxylic acid
ROX
TAMRA
Anthracene-isothiocyanate
Cy3
Cy3.5
Cy5
Cy5.5
Cy7
Cy7.5
Anilinonaphthalene-sulfonic acid

TABLE 3

Examples of Labeled Nucleoside Polyphosphates

Adenosine-5'-(γ-7-(9H-(1,3-dichloro-9,9-dimethylacridin-2-one)))triphosphate or A3P-DDAO
Guanosine-5'-(γ-7-(9H-(1,3-dichloro-9,9-dimethylacridin-2-one)))triphosphate or G3P-DDAO
Cytidine-5'-(γ-7-(9H-(1,3-dichloro-9,9-dimethylacridin-2-one)))triphosphate or C3P-DDAO
Thymidine-5'-(γ-7-(9H-(1,3-dichloro-9,9-dimethylacridin-2-one)))triphosphate or T3P-DDAO
Uridine-5'-(γ-7-(9H-(1,3-dichloro-9,9-dimethylacridin-2-one)))triphosphate or U3P-DDAO
2'-Deoxyadenosine-5'-(γ-7-(9H-(1,3-dichloro-9,9-dimethylacridin-2-one)))triphosphate or dA3P-DDAO
2'-Deoxyguanosine-5'-(γ-7-(9H-(1,3-dichloro-9,9-dimethylacridin-2-one)))triphosphate or dG3P-DDAO
2'-Deoxycytidine-5'-(γ-7-(9H-(1,3-dichloro-9,9-dimethylacridin-2-one)))triphosphate or dC3P-DDAO
2'-Deoxythymidine-5'-(γ-7-(9H-(1,3-dichloro-9,9-dimethylacridin-2-one)))triphosphate or dT3P-DDAO
2'-Deoxyuridine-5'-(γ-7-(9H-(1,3-dichloro-9,9-dimethylacridin-2-one)))triphosphate or dU3P-DDAO
Adenosine-5'-(δ-7-(9H-(1,3-dichloro-9,9-dimethylacridin-2-one)))tetraphosphate or A4P-DDAO
Guanosine-5'-(δ-7-(9H-(1,3-dichloro-9,9-dimethylacridin-2-one)))tetraphosphate or G4P-DDAO
Cytidine-5'-(δ-7-(9H-(1,3-dichloro-9,9-dimethylacridin-2-one)))tetraphosphate or C4P-DDAO
Thymidine-5'-(δ-7-(9H-(1,3-dichloro-9,9-dimethylacridin-2-one)))tetraphosphate or T4P-DDAO
Uridine-5'-(δ-7-(9H-(1,3-dichloro-9,9-dimethylacridin-2-one)))tetraphosphate or U4P-DDAO TABLE 3-continued Examples of Labeled Nucleoside Polyphosphates 2'-Deoxyadenosine-5'-(δ-7-(9H-(1,3-dichloro-9,9-dimethylacridin-2-one)))tetraphosphate or dA4P-DDAO
2'-Deoxyguanosine-5'-(δ-7-(9H-(1,3-dichloro-9,9-dimethylacridin-2-one)))tetraphosphate or dG4P-DDAO
2'-Deoxycytidine-5'-(δ-7-(9H-(1,3-dichloro-9,9-dimethylacridin-2-one)))tetraphosphate or dC4P-DDAO
2'-Deoxythymidine-5'-(δ-7-(9H-(1,3-dichloro-9,9-dimethylacridin-2-one)))tetraphosphate or dT4P-DDAO
2'-Deoxyuridine-5'-(δ-7-(9H-(1,3-dichloro-9,9-dimethylacridin-2-one)))tetraphosphate or dU4P-DDAO
Adenosine-5'-(ε-7-(9H-(1,3-dichloro-9,9-dimethylacridin-2-one)))pentaphosphate or A5P-DDAO
Guanosine-5'-(ε-7-(9H-(1,3-dichloro-9,9-dimethylacridin-2-one)))pentaphosphate or G5P-DDAO
Cytidine-5'-(ε-7-(9H-(1,3-dichloro-9,9-dimethylacridin-2-one))) pentaphosphate or C5P-DDAO
Thymidine-5'-(ε-7-(9H-(1,3-dichloro-9,9-dimethylacridin-2-one)))pentaphosphate or T5P-DDAO
Uridine-5'-(ε-7-(9H-(1,3-dichloro-9,9-dimethylacridin-2-one)))pentaphosphate or U5P-DDAO
2'-Deoxyadenosine-5'-(ε-7-(9H-(1,3-dichloro-9,9-dimethylacridin-2-one)))pentaphosphate or dA5P-DDAO
2'-Deoxyguanosine-5'-(ε-7-(9H-(1,3-dichloro-9,9-dimethylacridin-2-one)))pentaphosphate or dG5P-DDAO
2'-Deoxycytidine-5'-(ε-7-(9H-(1,3-dichloro-9,9-dimethylacridin-2-one)))pentaphosphate or dC5P-DDAO
2'-Deoxythymidine-5'-(ε-7-(9H-(1,3-dichloro-9,9-dimethylacridin-2-one)))pentaphosphate or dT5P-DDAO
2'-Deoxyuridine-5'-(ε-7-(9H-(1,3-dichloro-9,9-dimethylacridin-2-one)))pentaphosphate or dU5P-DDAO
Adenosine-5'-(ζ-7-(9H-(1,3-dichloro-9,9-dimethylacridin-2-one)))hexaphosphate or A6P-DDAO
Guanosine-5'-(ζ-7-(9H-(1,3-dichloro-9,9-dimethylacridin-2-one)))hexaphosphate or G6P-DDAO
Cytidine-5'-(ζ-7-(9H-(1,3-dichloro-9,9-dimethylacridin-2-one)))hexaphosphate or C6P-DDAO
Thymidine-5'-(ζ-7-(9H-(1,3-dichloro-9,9-dimethylacridin-2-one)))hexaphosphate or T6P-DDAO
Uridine-5'-(ζ-7-(9H-(1,3-dichloro-9,9-dimethylacridin-2-one)))hexaphosphate or U6P-DDAO
2'-Deoxyadenosine-5'-(ζ-7-(9H-(1,3-dichloro-9,9-dimethylacridin-2-one)))hexaphosphate or dA6P-DDAO
2'-Deoxyguanosine-5'-(ζ-7-(9H-(1,3-dichloro-9,9-dimethylacridin-2-one)))hexaphosphate or dG6P-DDAO
2'-Deoxycytidine-5'-(ζ-7-(9H-(1,3-dichloro-9,9-dimethylacridin-2-one)))hexaphosphate or dC6P-DDAO
2'-Deoxythymidine-5'-(ζ-7-(9H-(1,3-dichloro-9,9-dimethylacridin-2-one)))hexaphosphate or dT6P-DDAO
2'-Deoxyuridine-5'-(ζ-7-(9H-(1,3-dichloro-9,9-dimethylacridin-2-one)))hexaphosphate or dU6P-DDAO
Adenosine-5'-(γ-7-umbelliferone)triphosphate or A3P-Umb
Guanosine-5'-(γ-7-umbelliferone)triphosphate or G3P-Umb
Cytidine-5'-(γ-7-umbelliferone)triphosphate or C3P-Umb
Thymidine-5'-(γ-7-umbelliferone)triphosphate or T3P-Umb
Uridine-5'-(γ-7-umbelliferone)triphosphate or U3P-Umb
2'-Deoxyadenosine-5'-(γ-7-umbelliferone)triphosphate or dA3P-Umb
2'-Deoxyguanosine-5'-(γ-7-umbelliferone)triphosphate or dG3P-Umb
2'-Deoxycytidine-5'-(γ-7-umbelliferone)triphosphate or dC3P-Umb
2'-Deoxythymidine-5'-(γ-7-umbelliferone)triphosphate or dT3P-Umb
2'-Deoxyuridine-5'-(γ-7-umbelliferone)triphosphate or dU3P-Umb
Adenosine-5'-(δ-7-umbelliferone)tetraphosphate or A4P-Umb
Guanosine-5'-(δ-7-umbelliferone)tetraphosphate or G4P-Umb
Cytidine-5'-(δ-7-umbelliferone)tetraphosphate or C4P-Umb
Thymidine-5'-(δ-7-umbelliferone)tetraphosphate or T4P-Umb
Uridine-5'-(δ-7-umbelliferone)tetraphosphate or U4P-Umb
2'-Deoxyadenosine-5'-(δ-7-umbelliferone) tetraphosphate or dA4P-Umb
2'-Deoxyguanosine-5'-(δ-7-umbelliferone) tetraphosphate or dG4P-Umb
2'-Deoxycytidine-5'-(δ-7-umbelliferone) tetraphosphate or dC4P-Umb
2'-Deoxythymidine-5'-(δ-7-umbelliferone) tetraphosphate or dT4P-Umb
2'-Deoxyuridine-5'-(δ-7-umbelliferone) tetraphosphate or dU4P-Umb
Adenosine-5'-(ε-7-umbelliferone) pentaphosphate or A5P-Umb
Guanosine-5'-(ε-7-umbelliferone) pentaphosphate or G5P-Umb
Cytidine-5'-(ε-7-umbelliferone) pentaphosphate or C5P-Umb
Thymidine-5'-(ε-7-umbelliferone) pentaphosphate or T5P-Umb
Uridine-5'-(ε-7-umbelliferone) pentaphosphate or U5P-Umb
2'-Deoxyadenosine-5'-(ε-7-umbelliferone) pentaphosphate or dA5P-Umb
2'-Deoxyguanosine-5'-(ε-7-umbelliferone) pentaphosphate or dG5P-Umb
2'-Deoxycytidine-5'-(ε-7-umbelliferone) pentaphosphate or dC5P-Umb
2'-Deoxythymidine-5'-(ε-7-umbelliferone) pentaphosphate or dT5P-Umb
2'-Deoxyuridine-5'-(ε-7-umbelliferone) pentaphosphate or dU5P-Umb
Adenosine-5'-(ζ-7-umbelliferone)hexaphosphate or A6P-Umb
Guanosine-5'-(ζ-7-umbelliferone)hexaphosphate or G6P-Umb
Cytidine-5'-(ζ-7-umbelliferone)hexaphosphate or C6P-Umb
Thymidine-5'-(ζ-7-umbelliferone)hexaphosphate or T6P-Umb
Uridine-5'-(ζ-7-umbelliferone)hexaphosphate or U6P-Umb
2'-Deoxyadenosine-5'-(ζ-7-umbelliferone)hexaphosphate or dA6P-Umb
2'-Deoxyguanosine-5'-(ζ-7-umbelliferone)hexaphosphate or dG6P-Umb
2'-Deoxycytidine-5'-(ζ-7-umbelliferone)hexaphosphate or dC6P-Umb
2'-Deoxythymidine-5'-(ζ-7-umbelliferone)hexaphosphate or dT6P-Umb
2'-Deoxyuridine-5'-(ζ-7-umbelliferone)hexaphosphate or dU6P-Umb
Adenosine-5'-(γ-7-(4-methylumbelliferone))triphosphate or A3P-MeUmb
Guanosine-5'-(γ-7-(4-methylumbelliferone))))triphosphate or G3P-MeUmb
Cytidine-5'-(γ-7-(4-methylumbelliferone))triphosphate or C3P-MeUmb
Thymidine-5'-(γ-7-(4-methylumbelliferone))triphosphate or T3P-MeUmb
Uridine-5'-(γ-7-(4-methylumbelliferone))triphosphate or U3P-MeUmb
2'-Deoxyadenosine-5'-(γ-7-(4-methylumbelliferone))triphosphate or dA3P-MeUmb
2'-Deoxyguanosine-5'-(γ-7-(4-methylumbelliferone))triphosphate or dG3P-MeUmb
2'-Deoxycytidine-5'-(γ-7-(4-methylumbelliferone))triphosphate or dC3P-MeUmb
2'-Deoxythymidine-5'-(γ-7-(4-methylumbelliferone))triphosphate or dT3P-MeUmb
2'-Deoxyuridine-5'-(γ-7-(4-methylumbelliferone))triphosphate or dU3P-MeUmb
Adenosine-5'-(δ-7-(4-methylumbelliferone))tetraphosphate or A4P-MeUmb
Guanosine-5'-(δ-7-(4-methylumbelliferone))))tetraphosphate or G4P-MeUmb TABLE 3-continued Examples of Labeled Nucleoside Polyphosphates Cytidine-5'-(δ-7-(4-methylumbelliferone))tetraphosphate or C4P-MeUmb
Thymidine-5'-(δ-7-(4-methylumbelliferone))tetraphosphate or T4P-MeUmb
Uridine-5'-(δ-7-(4-methylumbelliferone))tetraphosphate or U4P-MeUmb
2'-Deoxyadenosine-5'-(δ-7-(4-methylumbelliferone)) tetraphosphate or dA4P-MeUmb
2'-Deoxyguanosine-5'-(δ-7-(4-methylumbelliferone)) tetraphosphate or dG4P-MeUmb
2'-Deoxycytidine-5'-(δ-7-(4-methylumbelliferone)) tetraphosphate or dC4P-MeUmb
2'-Deoxythymidine-5'-(δ-7-(4-methylumbelliferone)) tetraphosphate or dT4P-MeUmb
2'-Deoxyuridine-5'-(δ-7-(4-methylumbelliferone))tetraphosphate or dU4P-MeUmb
Adenosine-5'-(ε-7-(4-methylumbelliferone))pentaphosphate or A5P-MeUmb
Guanosine-5'-(ε-7-(4-methylumbelliferone))pentaphosphate or G5P-MeUmb
Cytidine-5'-(ε-7-(4-methylumbelliferone))pentaphosphate or C5P-MeUmb
Thymidine-5'-(ε-7-(4-methylumbelliferone))pentaphosphate or T5P-MeUmb
Uridine-5'-(ε-7-(4-methylumbelliferone))pentaphosphate or U5P-MeUmb
2'-Deoxyadenosine-5'-(ε-7-(4-methylumbelliferone))pentaphosphate or dA5P-MeUmb
2'-Deoxyguanosine-5'-(ε-7-(4-methylumbelliferone))pentaphosphate or dG5P-MeUmb
2'-Deoxycytidine-5'-(ε-7-(4-methylumbelliferone))pentaphosphate or dC5P-MeUmb
2'-Deoxythymidine-5'-(ε-7-(4-methylumbelliferone))pentaphosphate or dT5P-MeUmb
2'-Deoxyuridine-5'-(ε-7-(4-methylumbelliferone))pentaphosphate or dU5P-MeUmb
Adenosine-5'-(ζ-7-(4-methylumbelliferone))hexaphosphate or A6P-MeUmb
Guanosine-5'-(ζ-7-(4-methylumbelliferone))hexaphosphate or G6P-MeUmb
Cytidine-5'-(ζ-7-(4-methylumbelliferone))hexaphosphate or C6P-MeUmb
Thymidine-5'-(ζ-7-(4-methylumbelliferone))hexaphosphate or T6P-MeUmb
Uridine-5'-(ζ-7-(4-methylumbelliferone))hexaphosphate or U6P-MeUmb
2'-Deoxyadenosine-5'-(ζ-7-(4-methylumbelliferone))hexaphosphate or dA6P-MeUmb
2'-Deoxyguanosine-5'-(ζ-7-(4-methylumbelliferone))hexaphosphate or dG6P-MeUmb
2'-Deoxycytidine-5'-(ζ-7-(4-methylumbelliferone))hexaphosphate or dC6P-MeUmb
2'-Deoxythymidine-5'-(ζ-7-(4-methylumbelliferone))hexaphosphate or dT6P-MeUmb
2'-Deoxyuridine-5'-(ζ-7-(4-methylumbelliferone))hexaphosphate or dU6P-MeUmb
Adenosine-5'-(γ-7-resorufin)triphosphate or A3P-RR
Guanosine-5'-(γ-7-resorufin)))triphosphate or G3P-RR
Cytidine-5'-(γ-7-resorufin)triphosphate or C3P-RR
Thymidine-5'-(γ-7-resorufin)triphosphate or T3P-RR
Uridine-5'-(γ-7-resorufin)triphosphate or U3P-RR
2'-Deoxyadenosine-5'-(γ-7-resorufin) triphosphate or dA3P-RR
2'-Deoxyguanosine-5'-(γ-7-resorufin) triphosphate or dG3P-RR
2'-Deoxycytidine-5'-(γ-7-resorufin) triphosphate or dC3P-RR
2'-Deoxythymidine-5'-(γ-7-resorufin) triphosphate or dT3P-RR
2'-Deoxyuridine-5'-(γ-7-resorufin) triphosphate or dU3P-RR
Adenosine-5'-(δ-7-resorufin)tetraphosphate or A4P-RR
Guanosine-5'-(δ-7-resorufin)))tetraphosphate or G4P-RR
Cytidine-5'-(δ-7-resorufin)tetraphosphate or C4P-RR
Thymidine-5'-(δ-7-resorufin)tetraphosphate or T4P-RR
Uridine-5'-(δ-7-resorufin)tetraphosphate or U4P-RR
2'-Deoxyadenosine-5'-(δ-7-resorufin) tetraphosphate or dA4P-RR
2'-Deoxyguanosine-5'-(δ-7-resorufin) tetraphosphate or dG4P-RR
2'-Deoxycytidine-5'-(δ-7-resorufin) tetraphosphate or dC4P-RR
2'-Deoxythymidine-5'-(δ-7-resorufin) tetraphosphate or dT4P-RR
2'-Deoxyuridine-5'-(δ-7-resorufin) tetraphosphate or dU4P-RR
Adenosine-5'-(ε-7-resorufin)pentaphosphate or A5P-RR
Guanosine-5'-(ε-7-resorufin)pentaphosphate or G5P-RR
Cytidine-5'-(ε-7-resorufin)pentaphosphate or C5P-RR
Thymidine-5'-(ε-7-resorufin)pentaphosphate or T5P-RR
Uridine-5'-(ε-7-resorufin)pentaphosphate or U5P-RR
2'-Deoxyadenosine-5'-(ε-7-resorufin)pentaphosphate or dA5P-RR
2'-Deoxyguanosine-5'-(ε-7-resorufin)pentaphosphate or dG5P-RR
2'-Deoxycytidine-5'-(ε-7-resorufin) pentaphosphate or dC5P-RR
2'-Deoxythymidine-5'-(ε-7-resorufin) pentaphosphate or dT5P-RR
2'-Deoxyuridine-5'-(ε-7-resorufin) pentaphosphate or dU5P-RR
Adenosine-5'-(ζ-7-resorufin)hexaphosphate or A6P-RR
Guanosine-5'-(ζ-7-resorufin)hexaphosphate or G6P-RR
Cytidine-5'-(ζ-7-resorufin)hexaphosphate or C6P-RR
Thymidine-5'-(ζ-7-resorufin)hexaphosphate or T6P-RR
Uridine-5'-(ζ-7-resorufin)hexaphosphate or U6P-RR
2'-Deoxyadenosine-5'-(ζ-7-resorufin) hexaphosphate or dA6P-RR
2'-Deoxyguanosine-5'-(ζ-7-resorufin) hexaphosphate or dG6P-RR
2'-Deoxycytidine-5'-(ζ-7-resorufin)hexaphosphate or dC6P-RR
2'-Deoxythymidine-5'-(ζ-7-resorufin)hexaphosphate or dT6P-RR
2'-Deoxyuridine-5'-(ζ-7-resorufin)hexaphosphate or dU6P-RR
Adenosine-5'-(γ-3'-(6'-ethoxyfluorescein))triphosphate or A3P-FlEt
Guanosine-5'-(γ-3'-(6'-ethoxyfluorescein) triphosphate or G3P-FlEt
Cytidine-5'-(γ-3'-(6'-ethoxyfluorescein))triphosphate or C3P-FlEt
Thymidine-5'-(γ-3'-(6'-ethoxyfluorescein))triphosphate or T3P-FlEt
Uridine-5'-(γ-3'-(6'-ethoxyfluorescein))triphosphate or U3P-FlEt
2'-Deoxyadenosine-5'-(γ-3'-(6'-ethoxyfluorescein)) triphosphate or dA3P-FlEt
2'-Deoxyguanosine-5'-(γ-3'-(6'-ethoxyfluorescein)) triphosphate or dG3P-FlEt
2'-Deoxycytidine-5'-(γ-3'-(6'-ethoxyfluorescein)) triphosphate or dC3P-FlEt
2'-Deoxythymidine-5'-(γ-3'-(6'-ethoxyfluorescein)) triphosphate or dT3P-FlEt

TABLE 3-continued

Examples of Labeled Nucleoside Polyphosphates

2'-Deoxyuridine-5'-(γ-3'-(6'-ethoxyfluorescein)) triphosphate or dU3P-FlEt
Adenosine-5'-(δ-3'-(6'-ethoxyfluorescein))tetraphosphate or A4P-FlEt
Guanosine-5'-(δ-3'-(6'-ethoxyfluorescein))tetraphosphate or G4P-FlEt
Cytidine-5'-(δ-3'-(6'-ethoxyfluorescein))tetraphosphate or C4P-FlEt
Thymidine-5'-(δ-3'-(6'-ethoxyfluorescein))tetraphosphate or T4P-FlEt
Uridine-5'-(δ-3'-(6'-ethoxyfluorescein))tetraphosphate or U4P-FlEt
2'-Deoxyadenosine-5'-(δ-3'-(6'-ethoxyfluorescein)) tetraphosphate or dA4P-FlEt
2'-Deoxyguanosine-5'-(δ-3'-(6'-ethoxyfluorescein)) tetraphosphate or dG4P-FlEt
2'-Deoxycytidine-5'-(δ-3'-(6'-ethoxyfluorescein)) tetraphosphate or dC4P-FlEt
2'-Deoxythymidine-5'-(δ-3'-(6'-ethoxyfluorescein)) tetraphosphate or dT4P-FlEt
2'-Deoxyuridine-5'-(δ-3'-(6'-ethoxyfluorescein)) tetraphosphate or dU4P-FlEt
Adenosine-5'-(ε-3'-(6'-ethoxyfluorescein))pentaphosphate or A5P-FlEt
Guanosine-5'-(ε-3'-(6'-ethoxyfluorescein))pentaphosphate or G5P-FlEt
Cytidine-5'-(ε-3'-(6'-ethoxyfluorescein))pentaphosphate or C5P-FlEt
Thymidine-5'-(ε-3'-(6'-ethoxyfluorescein))pentaphosphate or T5P-FlEt
Uridine-5'-(ε-3'-(6'-ethoxyfluorescein))pentaphosphate or U5P-FlEt
2'-Deoxyadenosine-5'-(ε-3'-(6'-ethoxyfluorescein))pentaphosphate or dA5P-FlEt
2'-Deoxyguanosine-5'-(ε-3'-(6'-ethoxyfluorescein))pentaphosphate or dG5P-FlEt
2'-Deoxycytidine-5'-(ε-3'-(6'-ethoxyfluorescein))pentaphosphate or dC5P-FlEt
2'-Deoxythymidine-5'-(ε-3'-(6'-ethoxyfluorescein))pentaphosphate or dT5P-FlEt
2'-Deoxyuridine-5'-(ε-3'-(6'-ethoxyfluorescein))pentaphosphate or dU5P-FlEt
Adenosine-5'-(ζ-3'-(6'-ethoxyfluorescein))hexaphosphate or A6P-FlEt
Guanosine-5'-(ζ-3'-(6'-ethoxyfluorescein))hexaphosphate or G6P-FlEt
Cytidine-5'-(ζ-3'-(6'-ethoxyfluorescein))hexaphosphate or C6P-FlEt
Thymidine-5'-(ζ-3'-(6'-ethoxyfluorescein))hexaphosphate or T6P-FlEt
Uridine-5'-(ζ-3'-(6'-ethoxyfluorescein))hexaphosphate or U6P-FlEt
2'-Deoxyadenosine-5'-(ζ-3'-(6'-ethoxyfluorescein)) hexaphosphate or dA6P-FlEt
2'-Deoxyguanosine-5'-(ζ-3'-(6'-ethoxyfluorescein))hexaphosphate or dG6P-FlEt
2'-Deoxycytidine-5'-(ζ-3'-(6'-ethoxyfluorescein))hexaphosphate or dC6P-FlEt
2'-Deoxythymidine-5'-(ζ-3'-(6'-ethoxyfluorescein))hexaphosphate or dT6P-FlEt
2'-Deoxyuridine-5'-(ζ-3'-(6'-ethoxyfluorescein))hexaphosphate or dU6P-FlEt Wherein the phosphorylated label in Formula I is a fluorogenic moiety, it is desirably selected from one of the following (all shown as the phosphomonester): 2-(5'-chloro-2'-phosphoryloxyphenyl)-6-chloro-4-(3H)-quinazolinone, sold under the trade name ELF 97 (Molecular Probes, Inc.), fluorescein diphosphate (tetraammonium salt), fluorescein 3'(6')-O-alkyl-6'(3')-phosphate, 9H-(1,3-dichloro-9,9-dimethylacridin-2-one-7-yl)phosphate (diammonium salt), 4-methylumbelliferyl phosphate (free acid), resorufin phosphate, 4-trifluoromethylumbelliferyl phosphate, umbelliferyl phosphate, 3-cyanoubelliferyl phosphate, 9,9-dimethylacridin-2-one-7-yl phosphate, 6,8-difluoro-4-methylumbelliferyl phosphate and derivatives thereof.

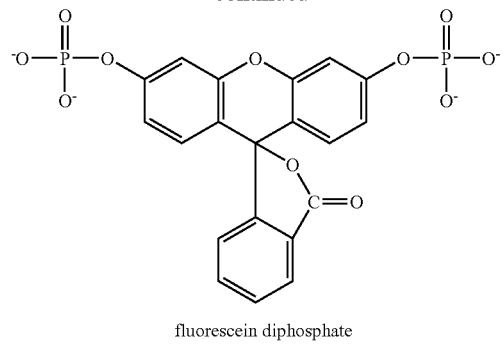

fluorescein diphosphate

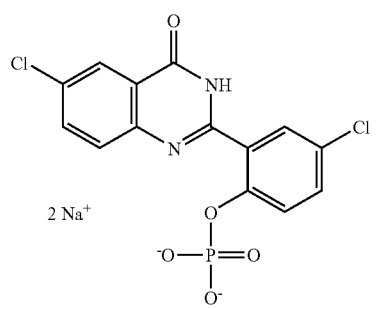

2-(5'-chloro-2'-phosphoryloxyphenyl)-6-chloro-4-(3H)-quinazolinone

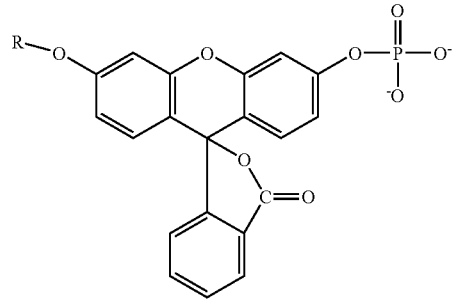

fluorescein 3'(6')-O-alkyl-6'(3')-phosphate

-continued

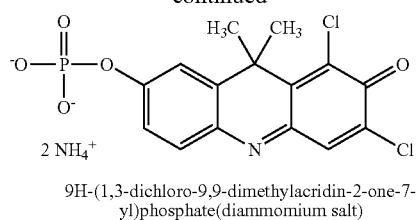

9H-(1,3-dichloro-9,9-dimethylacridin-2-one-7-yl)phosphate(diammomium salt)

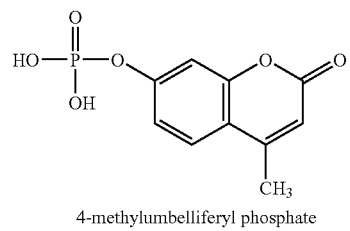

4-methylumbelliferyl phosphate

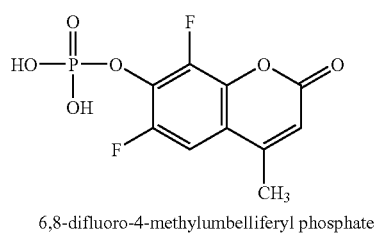

6,8-difluoro-4-methylumbelliferyl phosphate

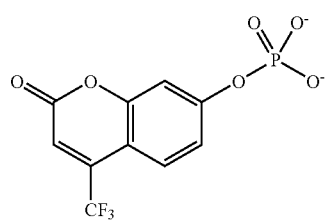

4-Trifluoromethylumbelliferyl phosphate

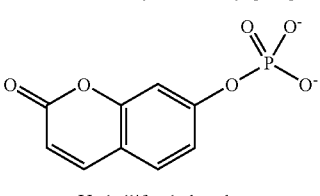

Umbelliferyl phosphate

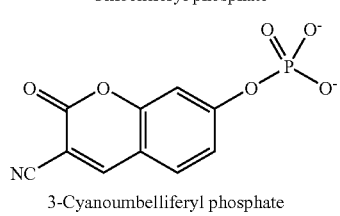

3-Cyanoumbelliferyl phosphate

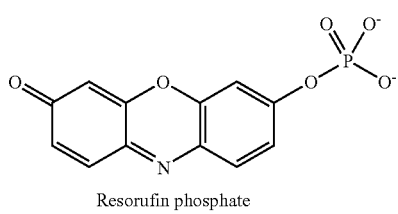

Resorufin phosphate

-continued

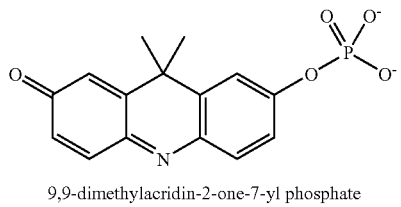

9,9-dimethylacridin-2-one-7-yl phosphate

Wherein the phosphorylated label moiety in Formula I above is a chromogenic moiety, it may be selected from the following: 5-bromo-4-chloro-3-indolyl phosphate, 3-indoxyl phosphate, p-nitrophenyl phosphate and derivatives thereof. The structures of these chromogenic dyes are shown as the phosphomonoesters below.

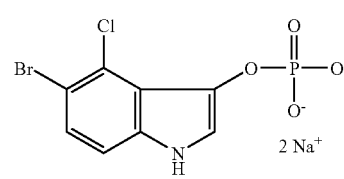

5-bromo-4-chloro-3-indolyl phosphate (disodium salt)

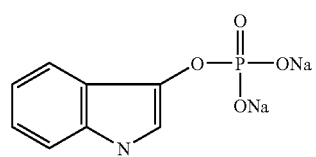

3-indolyl phosphate (disodium salt)

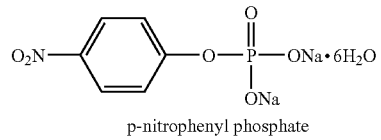

p-nitrophenyl phosphate

The moiety at the terminal-phosphate position may further be a chemiluminescent compound wherein it is desired that it is a phosphatase-activated 1,2-dioxetane compound. The 1,2-dioxetane compound may include, but is not limited to, disodium 2-chloro-5-(4-methoxyspiro[1,2-dioxetane-3, 2'-(5-chloro-)tricyclo[3,3,1-13,7]-decan]-1-yl)-1-phenyl phosphate, sold under the trade name CDP-Star (Tropix, Inc., Bedford, Mass.), chloroadamant-2'-ylidenemethoxyphenoxy phosphorylated dioxetane, sold under the trade name CSPD (Tropix), and 3-(2'-spiroadamantane)-4-methoxy-4-(3"-phosphoryloxy)phenyl-1,2-dioxetane, sold under the trade name AMPPD (Tropix). The structures of these commercially available dioxetane compounds are disclosed in U.S. Pat. Nos. 5,582,980, 5,112,960 and 4,978,614, respectively, and are incorporated herein by reference.

The methods described above may further include the step of quantifying the nucleic acid sequence. In a related aspect, the detectable species may be produced in amounts substantially proportional to the amount of an amplified nucleic acid sequence. The step of quantifying the nucleic acid sequence is desired to be done by comparison of spectra produced by the detectable species with known spectra.

Figure 6:
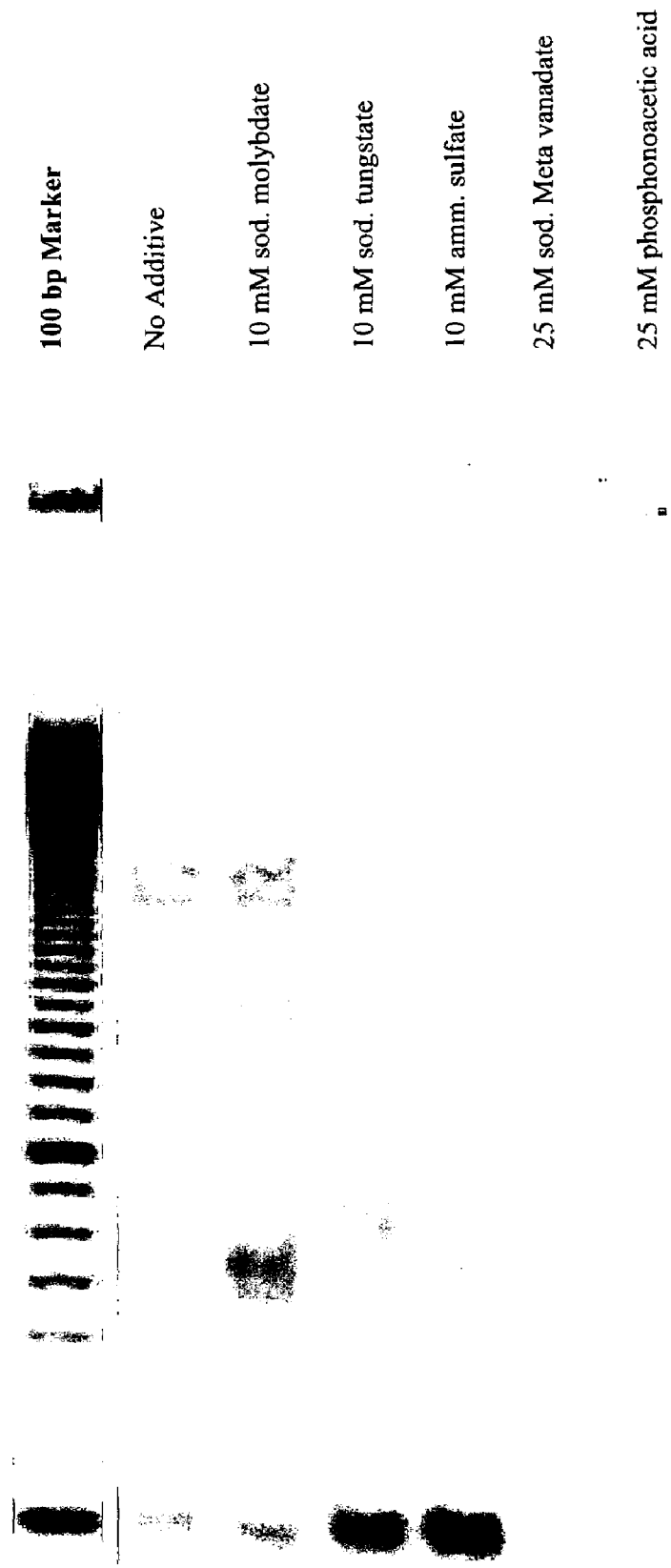
FIG. 6 shows PCR amplification with terminal-phosphate labeled nucleoside polyphosphates in the presence of stabilizers.

The present invention further provides a method of amplifying a nucleic acid sequence in the presence of a terminal-phosphate labeled nucleoside polyphosphate stabilizer such as polyol (glycerol, threitol, etc.), a polyether including cyclic polyethers, polyethylene glycol, organic or inorganic salts, such as ammonium sulfate, sodium sulfate, sodium molybdate, sodium tungstate, organic sulfonate, etc., in conjunction with a terminal-phosphate labeled nucleoside polyphosphate in the presence of a metal salt, such as manganese, magnesium, zinc, calcium or cobalt salts, to decrease the background signal generation in an enzymatic assay. Additives such as weak chelators have been used in the prior art during nucleic acid polymerization reactions in the presence of manganese. Their purpose, however was to reduce the rate of misincorporation of nucleotides caused by manganese. As shown in FIG. 6, even in the absence of additives, there is no misincorporation of the terminal-phosphate labeled nucleotides by polymerases. Hence, the purpose of adding additives in the current invention is solely to reduce non-enzymatic hydrolysis of terminal-phosphate labeled nucleotides caused by metal salts, to reduce background.

In one embodiment, the invention provides a method of quantifying a nucleic acid including the steps of: (a) conducting a nucleic acid amplification reaction, the amplification reaction including the reaction of at least one terminal-phosphate-labeled nucleotide, wherein the reaction results in the production of labeled polyphosphate; (b) permitting the labeled polyphosphate to react with a phosphatase to produce a detectable by-product species in an amount substantially proportional to the amount of the nucleic acid to be quantified; (c) measuring the detectable species; and (d) comparing the measurements using known standards to determine the quantity of the nucleic acid. In this embodiment of the method of quantifying a nucleic acid, the nucleic acid to be quantified may be RNA. The nucleic acid may further be a natural or synthetic oligonucleotide, chromosomal DNA, or DNA.

In another embodiment, the invention provides a method of quantifying a nucleic acid including the steps of: (a) conducting a nucleic acid amplification reaction in the presence of a manganese salt, the amplification reaction including the reaction of at least one terminal-phosphate-labeled nucleotide, wherein the reaction results in the production of labeled polyphosphate; (b) permitting the labeled polyphosphate to react with a phosphatase to produce a detectable by-product species in an amount substantially proportional to the amount of the nucleic acid to be quantified; (c) measuring the detectable species; and (d) comparing the measurements using known standards to determine the quantity of the nucleic acid.

The invention further provides a method of quantifying a DNA sequence including the steps of: (a) conducting a DNA amplification reaction in the presence of a terminal-phosphate-labeled nucleotide wherein the reaction results in the production of labeled polyphosphate; (b) permitting the labeled polyphosphate to react with a phosphatase to produce a detectable by-product species in amounts substantially proportional to the amount of the DNA sequence to be quantified; (c) measuring the detectable species; and (d) comparing measurements using known standards to determine the quantity of DNA. In this embodiment, the DNA sequence for quantification may include natural or synthetic oligonucleotides, or DNA isolated from cells including chromosomal DNA.

The invention further provides a method of quantifying a DNA sequence including the steps of: (a) conducting a DNA amplification reaction in the presence of a manganese salt and a terminal-phosphate-labeled nucleotide wherein the reaction results in the production of labeled polyphosphate; (b) permitting the labeled polyphosphate to react with a phosphatase to produce a detectable by-product species in amounts substantially proportional to the amount of the DNA sequence to be quantified; (c) measuring the detectable species; and (d) comparing measurements using known standards to determine the quantity of DNA.

In each of these methods of quantifying a nucleic acid sequence described above, the polymerase reaction step may further include conducting the polymerase reaction in the presence of a phosphatase. As described earlier in the specification, this would permit real-time monitoring of nucleic acid polymerase activity and hence, real-time detection of a target nucleic acid sequence for quantification.

The terminal-phosphate-labeled nucleotide useful for the methods of quantifying the nucleic acid sequence provided herein may be represented by Formula I shown above. The enzyme-activatable label becomes detectable through the enzymatic activity of phosphatase which changes the phosphate ester linkage between the label and the terminal-phosphate of a natural or modified nucleotide in such a way to produce a detectable species. The detectable species is detectable by the presence of any one of or a combination of color, fluorescence emission, chemiluminescence, mass difference or electrochemical potential. As already described above, the enzyme-activatable label may be a 1,2-dioxetane chemiluminescent compound, fluorescent dye, chromogenic dye, a mass tag or an electrochemical tag or a combination thereof. Suitable labels are the same as those described above.

Another aspect of the invention relates to a nucleic acid detection kit including:

(a) at least one or more terminal-phosphate-labeled nucleotide according to Formula I:

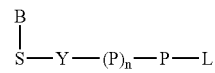

wherein P is phosphate (PO3) and derivatives thereof, n is 2 or greater; Y is an oxygen or sulfur atom; B is a nitrogen-containing heterocyclic base; S is a sugar moiety; L is a label containing a hydroxyl group, a sulfhydryl group, a haloalkyl group or an amino group suitable for forming a phosphate ester, a thioester, alkylphosphonate or a phosphoramidate linkage at the terminal phosphate of a natural or modified nucleotide; P-L is a phosphorylated label and may contain a linker between P and L; and (b) at least one nucleic acid polymerase.

Another aspect of the invention relates to a nucleic acid detection kit including:

(a) at least one or more terminal-phosphate-labeled nucleotide according to Formula I:

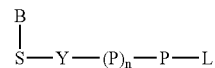

wherein P is phosphate (PO3) and derivatives thereof, n is 2 or greater; Y is an oxygen or sulfur atom; B is a nitrogen-containing heterocyclic base; S is a sugar moiety; L is a label containing a hydroxyl group, a sulfhydryl group, a haloalkyl group or an amino group suitable for forming a phosphate ester, a thioester, alkylphosphonate or a phosphoramidate linkage at the terminal phosphate of a natural or modified nucleotide; P-L is a phosphorylated label and may contain a linker between P and L;

(b) at least one nucleic acid polymerase; and
(c) a reaction buffer containing a manganese salt.

Another aspect of the invention relates to a nucleic acid detection kit including:

(a) at least one or more terminal-phosphate-labeled nucleotide according to Formula I:

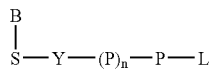

wherein P is phosphate (PO3) and derivatives thereof, n is 2 or greater; Y is an oxygen or sulfur atom; B is a nitrogen-containing heterocyclic base; S is a sugar moiety; L is a label containing a hydroxyl group, a sulfhydryl group, a haloalkyl group or an amino group suitable for forming a phosphate ester, a thioester, alkylphosphonate or a phosphoramidate linkage at the terminal phosphate of a natural or modified nucleotide; P-L is a phosphorylated label and may contain a linker between P and L;

(b) at least one nucleic acid polymerase;
(c) a reaction buffer containing a manganese salt; and
(d) a stabilizer Another aspect of the invention relates to a nucleic acid detection kit including:

(a) at least one or more terminal-phosphate-labeled nucleotide according to Formula I:

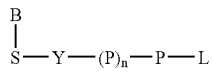

wherein P is phosphate (PO3) and derivatives thereof, n is 2 or greater; Y is an oxygen or sulfur atom; B is a nitrogen-containing heterocyclic base; S is a sugar moiety; L is an enzyme-activatable label containing a hydroxyl group, a sulfhydryl group or an amino group suitable for forming a phosphate ester, a thioester or a phosphoramidate linkage at the terminal phosphate of a natural or modified nucleotide; P-L is a phosphorylated label and may contain a linker between P and L; and (b) at least one nucleic acid polymerase.
(c) a phosphatase Another aspect of the invention relates to a nucleic acid detection kit including:

(a) at least one or more terminal-phosphate-labeled nucleotide according to Formula I below:

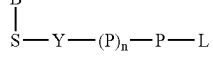

wherein P is phosphate (PO₃) and derivatives thereof, n is 2 or greater; Y is an oxygen or sulfur atom; B is a nitrogen-containing heterocyclic base; S is a sugar moiety; L is an enzyme-activatable label containing a hydroxyl group, a sulfhydryl group or an amino group suitable for forming a phosphate ester, a thioester or a phosphoramidate linkage at the terminal phosphate of a natural or modified nucleotide; P-L is a phosphorylated label which preferably becomes independently detectable when the phosphate is removed;

(b) at least one thermostable nucleic acid polymerase;
(c) a phosphatase; and
(d) reaction buffer containing a Manganese salt.

Another aspect of the invention relates to a nucleic acid detection kit including:

(a) at least one or more terminal-phosphate-labeled nucleotide according to Formula I:

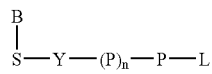

wherein P is phosphate (PO₃) and derivatives thereof, n is 2 or greater; Y is an oxygen or sulfur atom; B is a nitrogen-containing heterocyclic base; S is a sugar moiety; L is an enzyme-activatable label containing a hydroxyl group, a sulfhydryl group or an amino group suitable for forming a phosphate ester, a thioester or a phosphoramidate linkage at the terminal phosphate of a natural or modified nucleotide; P-L is a phosphorylated label which preferably becomes independently detectable when the phosphate is removed;

(b) at least one thermostable nucleic acid polymerase;
(c) a phosphatase;
(d) reaction buffer containing a Manganese salt; and
(e) a stabilizer.

Another aspect of the invention relates to a nucleic acid quantification kit including:

(a) at least one or more terminal-phosphate-labeled nucleotide according to Formula I:

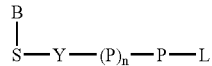

wherein P is phosphate (PO3) and derivatives thereof, n is 2 or greater; Y is an oxygen or sulfur atom; B is a nitrogen-containing heterocyclic base; S is a sugar moiety; L is an enzyme-activatable label containing a hydroxyl group, a sulfhydryl group or an amino group suitable for forming a phosphate ester, a thioester or a phosphoramidate linkage at the terminal phosphate of a natural or modified nucleotide; P-L is a phosphorylated label which preferably becomes independently detectable when the phosphate is removed;

(b) at least one thermostable nucleic acid polymerase; and
(c) phosphatase.

The sugar moiety in the terminal-phosphate-labeled nucleotide included in the kit may include, but is not limited to ribosyl, 2'-deoxyribosyl, 2'-alkoxyribosyl, 2'-aminoribosyl, 2'-fluororibosyl and other modified sugars.

The base may be, but is not limited to uracil, thymine, cytosine, 5-methylcytosine, guanine, 7-deazaguanine, hypoxanthine, 7-deazahypoxanthine, adenine, 7-deazaadenine and 2,6-diaminopurine and analogs thereof.

Furthermore, as described above, the enzyme-activatable label may be a 1,2-dioxetane chemiluminescent compound, fluorescent dye, chromogenic dye, a mass tag, an electrochemical tag or a combination thereof. Suitable compounds for conjugation at the terminal-phosphate position of the nucleotide are the same as those described above.

EXAMPLES

The following examples illustrate certain preferred embodiments of the illustration but are not intended to be illustrative of all embodiments.

Example 1

Preparation of δ-9H(1,3-dichloro-9,9-dimethylacridin-2-one-7-yl)-deoxythymidine-5'-tetraphosphate (dT4P-DDAO) and related compounds 10 μmoles TTP TEA salt was evaporated to dryness. To the residue was added 40 μmoles tributylamine and 5 ml dry pyridine. The solution was re-evaporated to dryness. After 2 coevaporations with 3 ml dry dimethylformamide (DMF), residue was re-dissolved in 200 μl dry DMF, flushed with argon and stoppered. Using a syringe, 50 μmoles (8 mg) carbonyldiimidazole (CDI) dissolved in 100 μl dry DMF was added. The flask was stirred for 4 hr at ambient temperature.

While the above reaction was progressing, 35 mg (83 μmoles) DDAO phosphate and 166 μmoles tributylamine were dissolved in dry DMF. The DDAO phosphate was evaporated to dryness followed by 3 coevaporations with dry DMF. Residue was dissolved in 300 μl dry DMF.

After the 4 hr reaction time, 3.2 μl anhydrous methanol was added to the TTP-CDI reaction. The reaction was stirred 30 minutes. To this mixture, DDAO phosphate solution was added and mixture was stirred at ambient temperature for 18 hr. The reaction was checked by Reverse phase HPLC (Xterra 4.6×100 column, 0.1M TEAA/acetonitrile). The reaction volume was reduced to 200 μl by evaporation and the reaction was allowed to progress for 80 hr.

After 80 hr, the reaction was stopped by adding 15 ml 0.1 M TEAB. The diluted mixture was applied to a 19×100 Xterra RP column and eluted with an acetonitrile gradient in 0.1M TEAB. The fractions containing pure DDAO T4P were evaporated to dryness and coevaporated twice with ethanol. The residue was reconstituted with MilliQ water. Yield: 1.10 μmole, 11%; HPLC purity >98% at 455 nm; MS: M-1=850.07 (calc. 849.95)

δ-9H(1,3-dichloro-9,9-dimethylacridin-2-one-7-yl)-deoxyguanosine-5'-tetraphosphate (dG4P-DDAO), δ-9H(1,3-dichloro-9,9-dimethylacridin-2-one-7-yl)-deoxycytidine-5'-tetraphosphate (dC4P-DDAO) and δ-9H(1,3-dichloro-9,9-dimethylacridin-2-one-7-yl)-deoxyadenosine-5'-tetraphosphate (dA4P-DDAO) were prepared in a similar manner as described above except 3.5 equivalents of DDAO phosphate was used instead of 8.3 equivalents. After C18 purification, samples were purified on ion exchange using a Mono Q 10/10 column.

δ-9H(1,3-dichloro-9,9-dimethylacridin-2-one-7-yl)-deoxyguanosine-5'-tetraphosphate (dG4P-DDAO): Yield 0.57 μmole, 5.7%; HPLC purity 99% at 455 nm; MS: M-1=875.03 (calc. 874.96).

δ-9H(1,3-dichloro-9,9-dimethylacridin-2-one-7-yl)-deoxycytidine-5'-tetraphosphate (dC4P-DDAO): Yield 0.24 μmole, 2.4%; HPLC purity 99% at 455 nm; MS: M-1=835.03 (calc. 834.95).

δ-9H(1,3-dichloro-9,9-dimethylacridin-2-one-7-yl)-deoxyadenosine-5'-tetraphosphate (dA4P-DDAO): Yield 0.38 μmole, 3.8%; HPLC purity 99% at 455 nm; MS: M-1=859.07 (calc. 858.97).

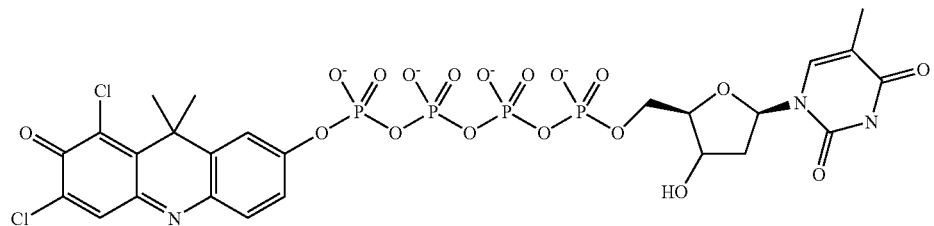

dT4P-DDAO

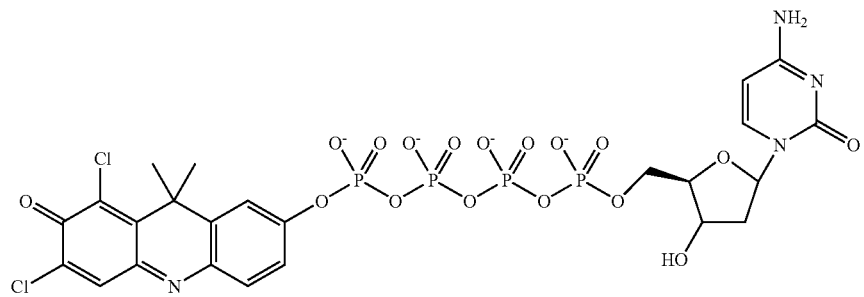

dC4P-DDAO

-continued

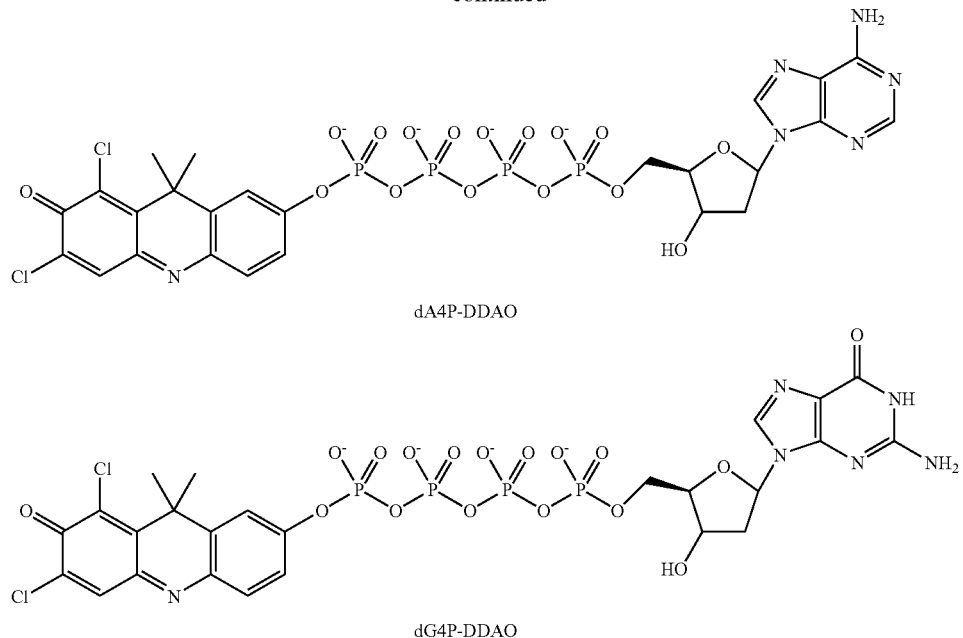

dA4P-DDAO dG4P-DDAO

Example 2

PCR Amplification of a Target Sequence Using Terminal-phosphate Labeled Nucleotide Polyphosphate Polymerase chain reaction (PCR) mixtures (20 µl) contained 20 mM Tris-HCL (pH 8.75), 10 mM KCL, 10 mM (NH$_4$)$_2$SO$_4$, 2 mM MgSO$_4$, 1 mg/ml bovine serum albumin and 0.1% (v/v) Triton X-100. The final nucleotide concentrations were 20 µM each, and 2.5 units of the DNA polymerase were used for each reaction. The initial template DNA (1–5 ng) was either pUC18 or pUCp53 (Amersham Biosciences). The sequences of the primers, along with the sequence of the amplified segment of pUCp53 are shown in Table 4. The initial amount of primer was 2 µmol each, and 2.5 units of the indicated DNA polymerase was used. Reactions were carried out for 15 thermal cycles of 90° C., 30 sec.; 55° C., 60 sec.; and 72° C., 300 sec. Most PCR reactions also included MnCl$_2$ at a final concentration of 0.08–0.2 mM. Reaction products were loaded onto 1.6% agarose gels. The gels were stained with SYBR Gold (Molecular Probes) according to the manufacturers' instructions and scanned at 532 nm using a Typhoon fluorescence scanner (Amersham Biosciences). Gel size markers were a 100 bp ladder (Amersham Biosciences).

The DNA polymerases used for these experiments included Taq DNA polymerase, Thermo Sequenase DNA polymerase (Amersham Biosciences), Tba exo-DNA polymerase (from Thermococcus barosii, U.S. Pat. No. 5,602,011 with D141A and E143A amino acid substitutions U.S. Pat. No. 5,882,904), Pfu DNA polymerase (Strategene), KOD XL DNA polymerase (Novagen) and Deep Vent DNA polymerase (New England BioLabs).

TABLE 4

| DNA Sequences | |
|---|---|
| PCR Product from pUCp53 | (SEQ ID NO: 1) |
| CTGTGCAGCT GTGGGTTGAT TCCACACCCC CGCCCGGCAC | 60 |
| CCGCGTCCGC GCCATGGCCA | |
| TCTACAAGCA GTCACAGCAC ATGACGGAGG TTGTGAGGCG CT | 102 |
| P53SNP22C-51F | (SEQ ID NO: 2) |
| CTGTGCAGCT GTGGGTTGAT TC | |
| P53SNP22G131R | (SEQ ID NO: 3) |
| AGCGCCTCAC AACCTCCGTC AT | |
| -21 Forward Primer | (SEQ ID NO: 4) |
| TGTAAAACGA CGGCCAGT | |

TABLE 4-continued

DNA Sequences

-28 Reverse Primer (SEQ ID NO: 5)

AGGAAACAGC TATGACCAT

FIG. 1 shows the results of PCR using several DNA polymerases and either normal nucleotides (lanes 10–12) or a mixture of dATP, dGTP, dCTP and □-DDAO dT tetra Phosphate (DDAO-dT4P). For this experiment, either Taq DNA polymerase (lanes 1–3, 12), Thermo Sequenase (Amersham Biosciences) DNA polymerase (lanes 7–9, 11) or Tba exo-DNA polymerase (lanes 4–6, 10) were used. The $MnCl_2$ concentration was 0 mM for the reactions resolved in lanes 1, 4, 7 and 10–12; 0.2 mM in lanes 2, 5, and 8; 0.4 mM in lanes 3, 6 and 9. For all samples, the template DNA was pUCp53 and the primers were P53SNP22C-51F and P53SNP22G131R. As shown in the figure, significant amounts of PCR product were made by all three polymerases using normal nucleotides, but only by the Tba exo-polymerase when DDAO-dT4P replaced dTTP, and that PCR yield is increased at least 5-fold in the presence of 0.2–0.4 mM $MnCl_2$. In similar experiments (not shown), it was found that product yield is increased with as little as 0.04 mM $MnCl_2$, and as much as 1.0 mM $MnCl_2$. It is interesting to note that $MnCl_2$ is not required when normal dNTPs are used, and in fact $MnCl_2$ reduces the yield of these PCR amplifications (data not shown). In addition, PCR product is made by Pfu DNA polymerase and by KOD XL DNA polymerase under the same conditions. It is also interesting to note that the failure of some polymerases to make amplification products suggests that the successful amplification by Tba exo-DNA polymerase and other polymerases was not achieved by simple breakdown of the phosphate-modified nucleotide.

Example 3

Detection of PCR Products by Fluorescence.

Shrimp alkaline phosphatase (Amersham Biosciences), 0.1 unit, was added to the products of the reactions displayed in lanes 2 and 5 of FIG. 1 and incubated at 37° C. for 30 minutes. Then the fluorescence was determined using a FarCYte fluorescence plate reader (Amersham Biosciences) using 650 nm excitation and 670 nm emission. The reaction product of Taq polymerase (producing little or no detectable PCR product) gave a reading of 5500 fluorescence units. The reaction product of Tba exo-DNA polymerase gave a reading of 31,000 fluorescence units. This indicates that simple fluorescence readings detecting the free DDAO fluorescence can be used to detect successful PCR amplification.

Example 4

PCR with Additional Nucleotides, Templates and Primers.

Figure 2:
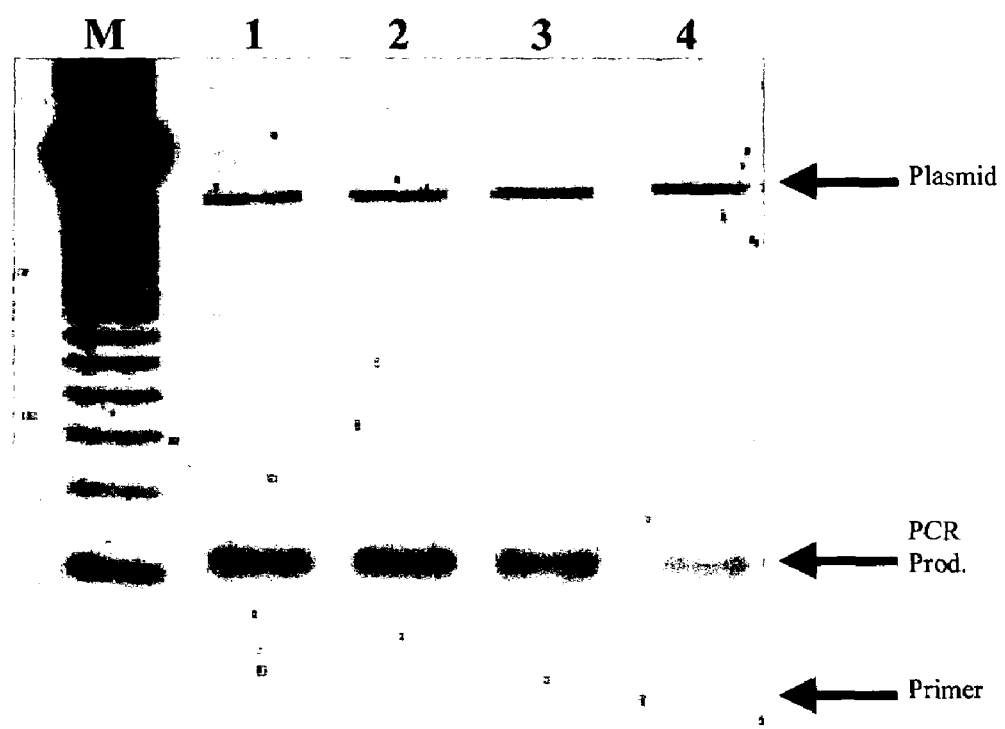
FIG. 2 shows PCR amplification of pUCp53 DNA using terminal-phosphate labeled nucleoside polyphosphates with different labels or bases.
Figure 3:
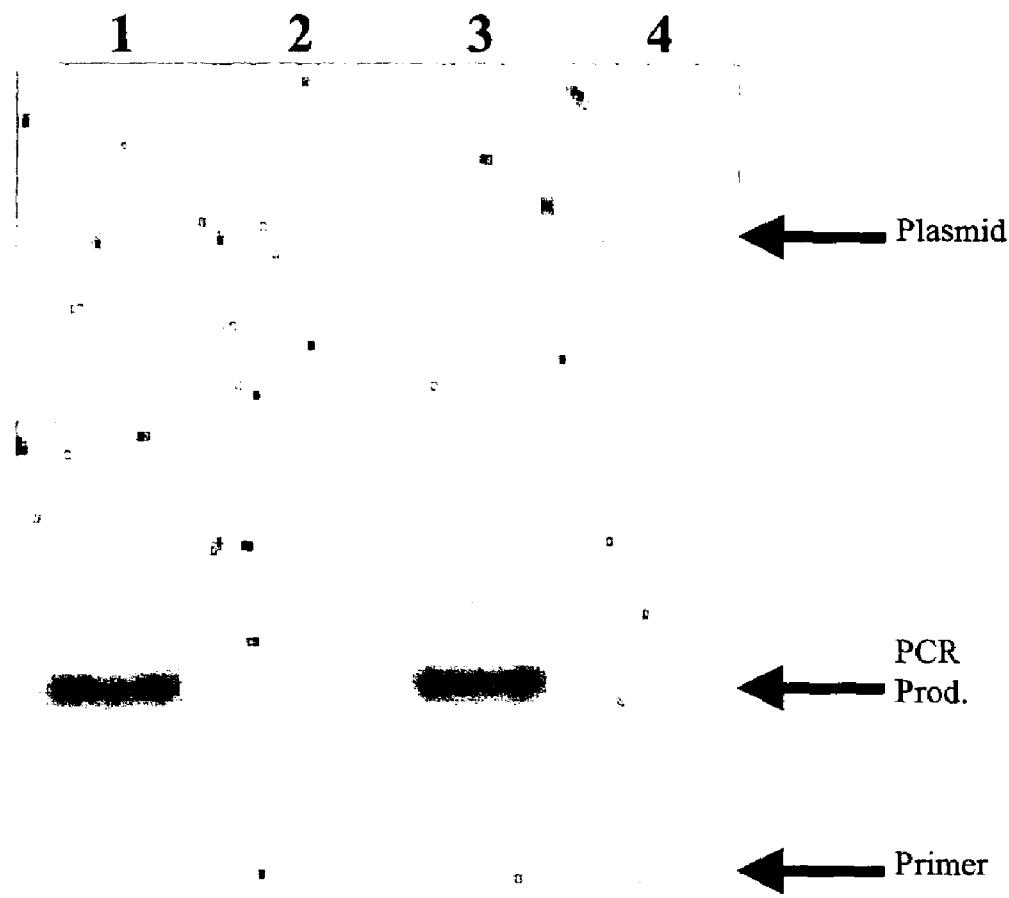
FIG. 3 shows PCR amplification of pUC18 DNA using terminal-phosphate labeled nucleoside polyphosphates with different labels or bases.

FIG. 2 shows the products of amplification of the same template as for FIG. 1 with the same primers. FIG. 3 shows the products of amplification of pUC 18 DNA using −21 Forward and −28 Reverse primers (Table 1). For both figures, the amplification reaction loaded in lane 1 was performed with normal dNTPs and without $MnCl_2$. For the lanes marked 2, the dTTP was replaced by dT4P-DDAO and the reactions contained 0.2 mM $MnCl_2$. For the lanes marked 3, the dGTP was replaced by dG4P-DDAO, and for the lanes marked 4, the dGTP was replaced by dG4P-MeCoumarin again with 0.2 mM $MnCl_2$. All amplifications successfully produced product of the expected size, suggesting that amplification is independent of the base or dye moiety in the modified nucleotides.

Example 5

Effect of Additives on Non-enzymatic Hydrolysis of Terminal-phosphate Labeled Nucleoside Polyphosphates Seventy μl samples containing 50 mM Hepes, pH 8.0, 5 mM $MgCl_2$, 0.5 mM $MnCl_2$, 0.01% Tween-20, 1 μm ddT4P-EtFl, 100 nM primer/template, 0.0036 units/μl SAP with or without 5% glycerol were cycled as follows: 95° C., 30 sec and 50° C., 3 min, repeat 10 times. Amount of free dye formed was checked in a fluorimeter. In the absence of glycerol concentration of free dye formed was 151 nM compared to only 19 nM in the presence of glycerol (close to the value observed in the absence of manganese, 8 nM). Clearly at high temperatures glycerol reduces the amount of degradation caused by manganese.

Example 6

Effect of Ammonium Sulfate as an Additive on Non-enzymatic Hydrolysis of Terminal-phosphate Labeled Nucleoside Polyphosphates in the Presence of $MnCl_2$.

Figure 4:
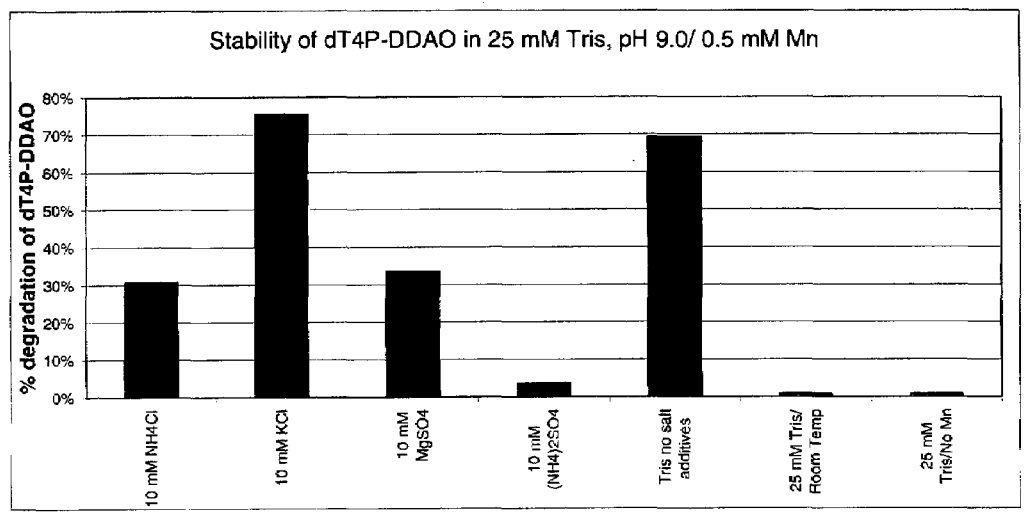
FIG. 4 shows stabilization of dT4P-DDAO with ammonium sulfate.

Twenty μl of 25 mM Tris.HCl, pH 9.0 containing 0.5 mM $MnCl_2$, 1 μm dT4P-DDAO and 10 mM salt (see FIG. 4) were heated at 95° C. for 60 minutes. Four μl of each reaction mix was mixed with 16 μl of BAP solution in Hepes (0.005 units BAP/μl) and incubated at 37° C. for 60 minutes. Samples were read on Tecan ultra plate reader. Un heated sample and unheated sample without $MnCl_2$ were used as controls. Raw fluorescence counts were converted into % degradation by using fluorescence counts from a Snake Venom phosphodiesterase hydrolyzed sample as 100% degraded sample. FIG. 4 clearly shows that addition of ammonium sulfate clearly stabilizes the dT4P-DDAO. Some stabilization effect is also observed in the presence of sulfate ions ($MgSO_4$) and ammonium ions ($NH_4Cl$).

Example 7

Effect of Other Salts as Additives on Non-enzymatic Hydrolysis of Terminal-phosphate Labeled Nucleoside Polyphosphates in the Presence of $MnCl_2$.

Figure 5:
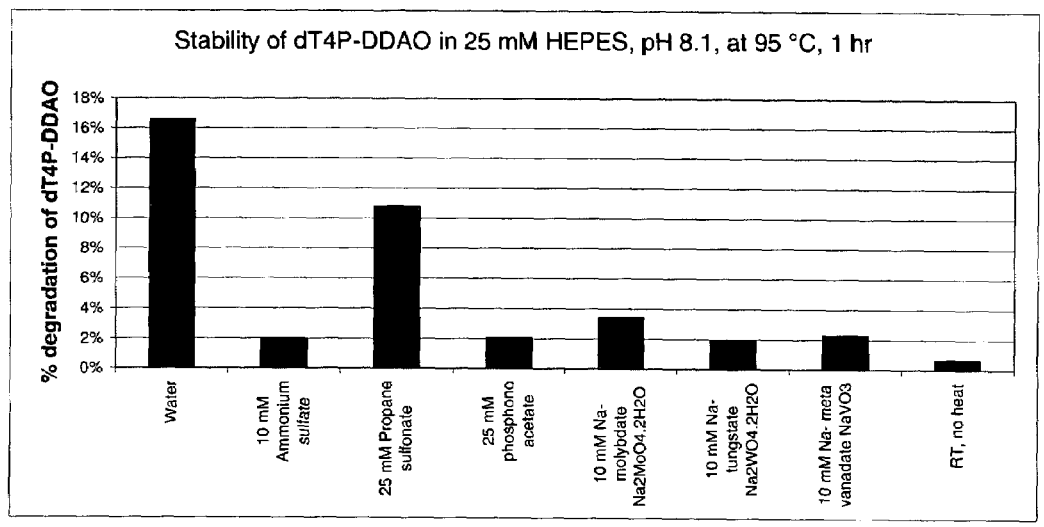
FIG. 5 shows stabilization of dT4P-DDAO with a variety of organic and inorganic salts.

Twenty μl of 25 mM Hepes, pH 8.1, containing 0.5 mM $MnCl_2$, 1 μm dT4P-DDAO and 10 or 25 mM inorganic or organic salt (see FIG. 5) was heated at 95° C. for 60 minutes. 4 μl of each sample was treated with BAP as described above and read on Tecan ultra plate reader. An unheated sample with $MnCl_2$ (water lane) and a heated sample without Hepes and $MnCl_2$ were used as controls. Fluorescence counts were converted into % degradation as described above. Data in FIG. 5 clearly shows that ammonium sulfate, phosphonoacetate, sodium molybdate, sodium tungstate and sodium vanadate stabilize the nucleotide. Stabilization due to propane sulfonate on the other hand was minimal.

Example 8

PCR Amplification Using Terminal Phosphate Labeled Nucleoside Polyphosphates in the Presence of Nucleotide Stabilizing Additives.

Polymerase chain reaction (PCR) mixtures (20 µl) contained 25 mM Hepes (pH 8.1), 10 mM KCl, 2 mM MgSO$_4$, 0.25 mM MnCl$_2$, 1 mg/ml bovine serum albumin, 0.01% (v/v) Tween-20 and 10–25 mM salt as shown in FIG. 6. Each sample also contained 20 µm each of dA4P-Me, dT4P-Me, dC4P-Me, 200 µm dG4P-FlEt, 0.006 units/µl BAP, 2 units of T. ba polymerase, 0.1 µm −40 M13 forward primer, 0.1 µm −28 M13 reverse primer and 0.2 ng M13 DNA. In addition to the terminal-phosphate labeled nucleotide, terminal methyl-blocked dNTP's were used instead of normal dNTP's to prevent degradation by BAP (phosphatase). Latter is required for signal generation from dye-polyphosphate after the nucleotide is incorporated into DNA by polymerase. Reactions were carried out for 35 thermal cycles of 90° C., 30 sec.; 55° C., 30 sec.; and 65° C., 300 sec. Reaction products were loaded onto 1.6% agarose gels. The gels were stained with SYBR Gold (Molecular Probes) according to the manufacturers' instructions and scanned at 532 nm using a Typhoon fluorescence scanner (Amersham Biosciences). Gel size markers were a 100 bp ladder (Amersham Biosciences).

As shown in FIG. 6, PCR product was separated in the presence of ammonium sulfate, sodium molybdate and sodium tungstate as well as in the absence of any stabilizer. No product formed in the presence of sodium meta vanadate or phosphonoacetate. Considering that ammonium sulfate, sodium molybdate and tungstate not only stabilize terminal-phosphate labeled nucleoside polyphosphates but also allow DNA amplification, these salts are quite useful for use in quantitative amplification methods.

Example 9

Quantitative PCR Using Terminal-phosphate Labeled Nucleoside Polyphosphates.

Figure 7:
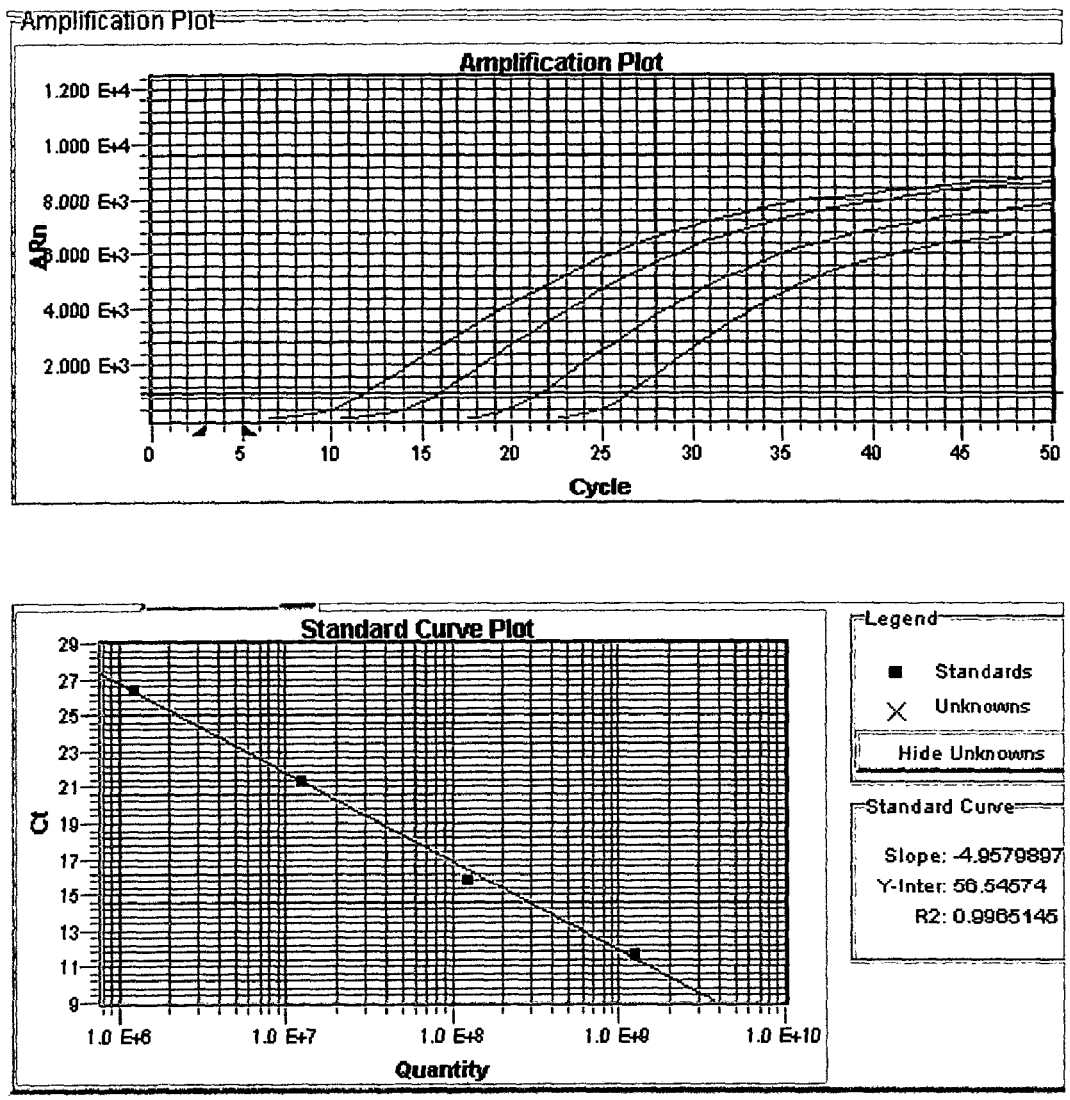
FIG. 7 shows quantitative PCR results with terminal-phosphate labeled nucleoside polyphosphates on ABI 7900 instrument.

Polymerase chain reaction (PCR) mixtures (20 µl) contained 25 mM Tris.HCl (pH 9.0), 10 mM KCl, 2 mM MgSO$_4$, 0.25 mM MnCl$_2$, 1 mg/ml bovine serum albumin and 0.01% (v/v) Tween-20. Each sample also contained 20 µm each of dA4P-Me, dT4P-Me, dC4P-Me, 200 µm dG4P-FlEt, 0.005 units/µl BAP, 2 units of pfu (with A486Y mutation) polymerase, 0.1 µm −40 M13 forward primer, 0.1 µM −28 M13 reverse primer and $1.2 \times 10^{6-1.2 \times 10^9}$ copies of M13 DNA. In addition to the terminal-phosphate labeled nucleotide, the remaining nucleotides were blocked with a methyl group on the terminal phosphate to prevent degradation by BAP. Reactions were carried out for 50 thermal cycles of 90° C., 30 sec.; 55° C., 30 sec.; and 65° C., 300 sec on ABI 7900 instrument. Cycle count at which the fluorescence count reaches a certain threshold (corresponding to a fixed amount of amplification product) for each reaction was plotted against the amount of input M13 DNA copies to give a straight line (FIG. 7) indicating that the method can be used for the quantification of target DNA copy number in a given sample.

Figure 8:
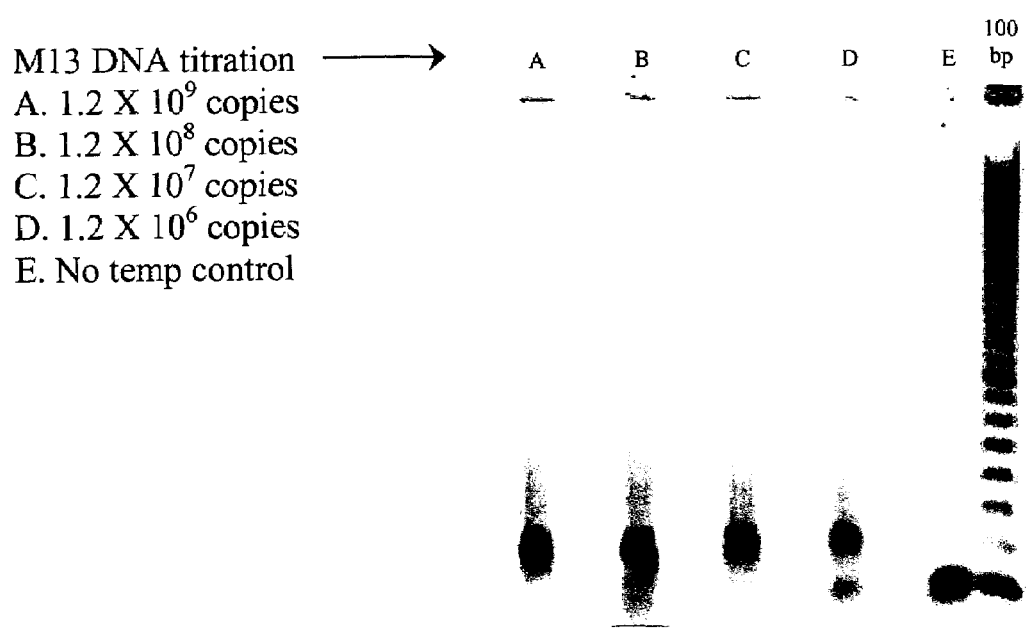
FIG. 8 shows PCR product produced during quantitative PCR using terminal-phosphate labeled nucleoside polyphosphate.

Reaction products were also loaded onto 1.6% agarose gels. The gels were stained with SYBR Gold (Molecular Probes) according to the manufacturers' instructions and scanned at 532 nm using a Typhoon fluorescence scanner (Amersham Biosciences) to show the formation of PCR product (FIG. 8). Gel size markers were a 100 bp ladder (Amersham Biosciences).

Example 10

DNA amplification by Rolling Circle Amplification (RCA) using terminal-phosphate labeled/blocked nucleoside polyphosphates Varying amounts of denatured salmon sperm chromosomal DNA was taken in 25 mM Tris: borate buffer, pH 8.0, containing 5 mM ammonium sulfate, 75 mM NaCl, 5 mM MgCl2, 1 mM MnSO4, 0.01% Tween-20, 400 ng Phi29 DNA polymerase, 40 µm nuclease resistant random hexamers, 0.03 units of BAP and 50 µm each of dA4P-Me, dG4P-Me, dC4P-Me and dT4P-DDAO. Reactions were incubated at 30° C. in a Tecan fluorescent plate reader and were read every five minutes at excitation and emission wavelengths optimized for DDAO. Raw fluorescence counts are plotted as a function of time.

Figure 9:
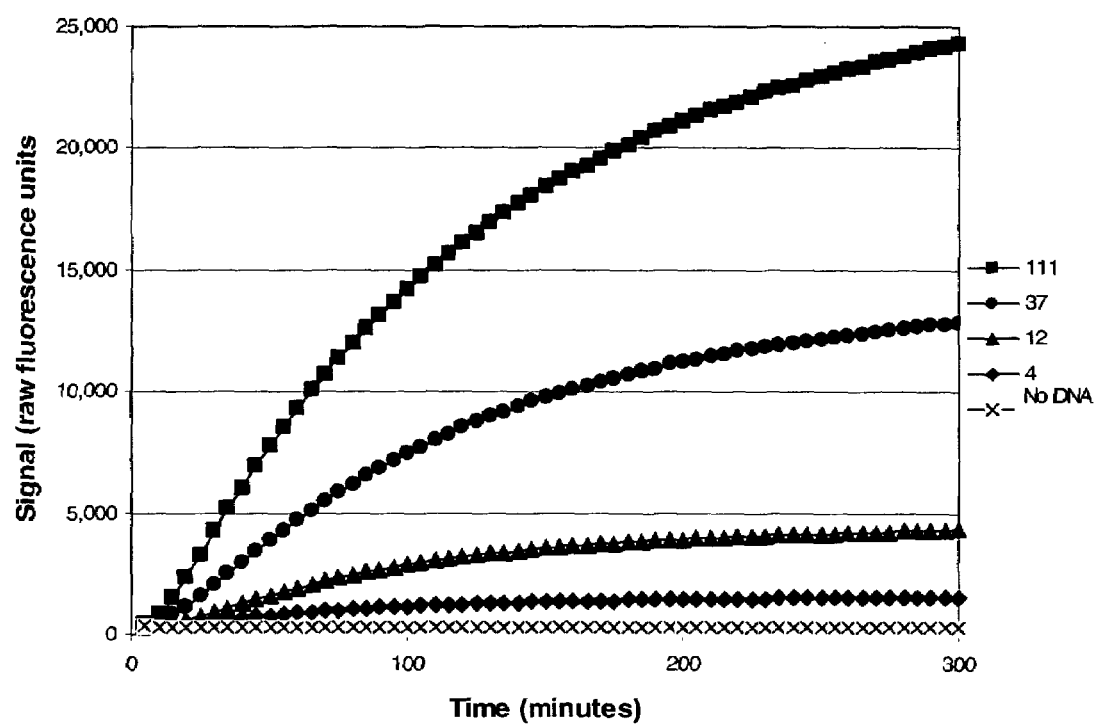
FIG. 9 shows linear amplification of chromosomal DNA using terminal-phosphate labeled nucleoside polyphosphates and Phi29 DNA polymerase.
Figure 10:
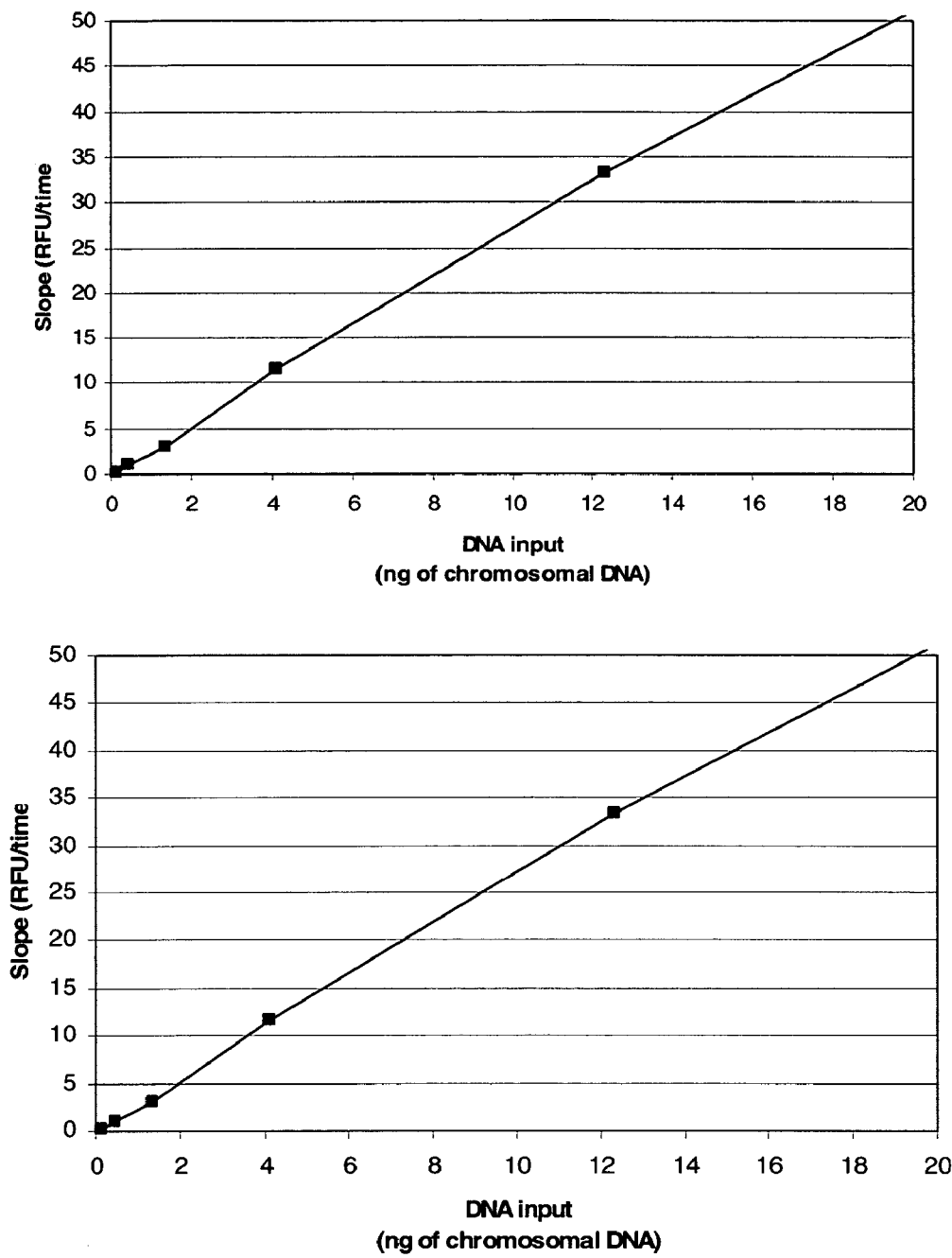
FIG. 10 shows that the amount of product produced in the initial phase of amplification is directly proportional to the amount of input DNA.

FIG. 9 clearly shows that in the absence of input DNA, no signal is produced. As the amount of DNA increases, the amount of fluorescence and hence the amount of product produced, increases. Furthermore, when the slope from the linear phase of amplification for each reaction (between 20–40 minutes) is plotted as a function of DNA input (FIG. 10), a linear correlation, between the amount of input DNA and the rate of product formation, is observed, indicating that this method can be used for quantifying DNA.

Having described the particular, desired embodiments of the invention herein, it should be appreciated that modifications may be made therethrough without departing from the contemplated scope of the invention. The true scope of the invention is set forth in the claims appended hereto.

What is claimed is:

1. In a method for nucleic acid amplification, which includes a polymerase reaction of a nucleic acid template, a primer, a nucleic acid polymerase, and at least one nucleoside polyphosphate, the improvement comprising conducting said polymerase reaction in the presence of at least one terminally labeled nucleoside polyphosphate, and wherein the amplification is conducted in the presence of a stabilizer that stabilizes the terminal-phosphate labeled nucleoside polyphosphate against non-enzymatic hydrolysis.

2. The method of claim 1, wherein said stabilizer is an organic additive, an inorganic additive, or a mixture of the two.

3. The method of claim 2, wherein said organic additive is an organic salt.

4. The method of claim 2, wherein said inorganic additive is an inorganic salt.

5. The method of claim 4, wherein said inorganic salt is selected from sulfates, molybdates, tungstates or a combination thereof.

6. In a method for nucleic acid amplification, which includes a polymerase reaction of a nucleic acid template, a primer, a nucleic acid polymerase, and at least one nucleoside polyphosphate, the improvement comprising conducting said polymerase reaction in the presence of at least one terminally labeled nucleoside polyphosphate, and wherein said terminal-phosphate labeled nucleoside polyphosphate comprises four or more phosphate groups in the polyphosphate chain.

7. A method of detecting the presence of a nucleic acid sequence in a sample comprising the steps of:

(a) conducting a nucleic acid amplification reaction to generate a labeled polyphosphate, said reaction including at least one terminal-phosphate labeled nucleoside polyphosphate, and a nucleic acid polymerase; and (b) detecting said labeled polyphosphate;

wherein said detecting step includes (a) treating said labeled polyphosphate with a phosphatase to produce a detectable species; and (b) detecting said detectable species.

8. The method of claim 7, wherein amplification is conducted in the presence of two or more terminal-phosphate labeled nucleoside polyphosphates with distinct labels.

9. The method of claim 7, wherein said treating step and said conducting step are performed simultaneously.

10. The method of claim 9, wherein said detecting step is performed in real time as said detectable species is produced.

11. The method of claim 7, wherein said nucleic acid polymerase is selected from the group consisting of a DNA polymerase, an RNA polymerase, a reverse transcriptase, a telomerase, a primase or a terminal nucleotidyl transferase.

12. The method of claim 7, wherein said phosphatase is an alkaline phosphatase or an acid phosphatase.

13. The method of claim 12, wherein said alkaline phosphatase is selected from the group consisting of *E. coli* alkaline phosphatase, calf intestine alkaline phosphatase, Shrimp alkaline phosphatase and *Rhodothermus marinus* alkaline phosphatase.

14. The method of claim 7, wherein the amplification is achieved by PCR, RCA, SDA, or NASBA.

15. The method of claim 7, wherein said conducting step is performed by PCR, and said reaction further includes allele specific primers.

16. The method of claim 7, wherein said terminal-phosphate labeled nucleoside polyphosphate is represented by the formula:

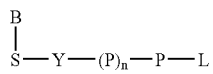

wherein P is phosphate ($PO_3$) and derivatives thereof; n is 2 or greater; Y is an oxygen or sulfur atom; B is a nitrogen-containing heterocyclic base; S is a sugar moiety; L is an enzyme-activatable label containing a hydroxyl group, a sulfhydryl group or an amino group suitable for forming a phosphate ester, a thioester or a phosphoramidate linkage at the terminal phosphate of a natural or modified nucleotide; P-L is a phosphorylated label.

17. The method of claim 16, wherein said terminal-phosphate labeled nucleoside polyphosphate contains a linker between P and L.

18. The method of claim 16, wherein said phosphorylated label is an enzyme-activatable label and is selected from the group consisting of chemiluminescent compounds, fluorogenic dyes, chromogenic dyes, mass tags, electrochemical tags and combinations thereof.

19. The method of claim , wherein said enzyme-activatable label is a fluorogenic moiety selected from the group consisting of 2-(5'-chloro-2'-phosphoryloxyphenyl)-6-chloro-4-(3H)-quinazolinone, fluorescein diphosphate, fluorescein 3'(6')-O-alkyl-6'(3')-phosphate, 9H-(1,3-dichloro-9,9-dimethylacridin-2-one-7-yl)phosphate, 4-methylumbelliferyl phosphate, resorufin phosphate, 4-trifluoromethylumbelliferyl phosphate, umbelliferyl phosphate, 3-cyanoumbelliferyl phosphate, 9,9-dimethylacirdin-2-one-7-yl phosphate, and 6,8-difluoro-4-methylumbelliferyl phosphate.

20. The method of claim 18, wherein said enzyme-activatable label is a chromogenic moiety selected from the group consisting of 5-bromo-4-chloro-3-indolyl phosphate, 3-indoxyl phosphate, and p-nitrophenyl phosphate.

21. The method of claim 18, wherein said chemiluminescent compound is an alkaline phosphatase-activated 1,2-dioxetane compound.

22. The method of claim 21, wherein said 1,2-dioxetane compound is selected from the group consisting of 2-chloro-5-(4-methoxyspiro[1,2-dioxetane-3,2'-(5-chloro-)tricyclo[3,3,1-1$^{3,7}$]-decan]-1-yl)-1-phenyl phosphate, chloroadamant-2'-ylidenemethoxyphenoxy phosphorylated dioxetane, and 3-(2'-spiroadamantane)-4-methoxy-4-(3"-phosphoryloxy)phenyl-1,2-dioxetane.

23. A kit for amplifying or quantifying a nucleic acid target comprising:

(a) at least one terminal-phosphate labeled nucleotide;

(b) a polymerase; and (c) a phosphatase.

24. A kit for amplifying or quantifying a nucleic acid target comprising:

(a) at least one terminal-phosphate labeled nucleotide;

(b) a polymerase; and (c) a terminal-phosphate labeled nucleoside polyphosphate stabilizer.

25. The kit as in claim 23, further including a manganese salt.

26. The kit as in claim 23, further including a set of random-sequence primers.

27. The kit as in claim 26, wherein the primers are of length 4–10 nucleotides.

28. The kit as in claim 26, wherein the primers are hexamers.

29. The kit as in claim 26, wherein the primers are nuclease resistant.

30. A method of detecting the presence of a nucleic acid sequence in a sample comprising the steps of:

(a) conducting an exponential DNA amplification reaction to generate a labeled polyphosphate, said reaction including at least one terminal-phosphate labeled nucleoside polyphosphate, and a nucleic acid polymerase; and (b) detecting said labeled polyphosphate;

wherein said terminal-phosphate labeled nucleoside polyphosphate comprises four or more phosphate groups in the polyphosphate chain.

* * * * *

UNITED STATES PATENT AND TRADEMARK OFFICE
CERTIFICATE OF CORRECTION

| | |
|---|---|
| PATENT NO. | : 7,125,671 B2 |
| APPLICATION NO. | : 10/651362 |
| DATED | : October 24, 2006 |
| INVENTOR(S) | : Anup Sood |

Page 1 of 1

It is certified that error appears in the above-identified patent and that said Letters Patent is hereby corrected as shown below:

Column 37,
Line 57, in claim 19, after "The method of claim" add -- 18 --.

Signed and Sealed this

Third Day of July, 2007

JON W. DUDAS
*Director of the United States Patent and Trademark Office*